(12) United States Patent
Peso et al.

(10) Patent No.: US 11,175,522 B2
(45) Date of Patent: Nov. 16, 2021

(54) ADVANCED LIQUID CRYSTAL FILM FOR ANTI MOTION SICKNESS AND METHODS THEREOF

(71) Applicant: GAUZY LTD, Tel Aviv (IL)

(72) Inventors: Eyal Peso, Bat Yam (IL); Adrian Lofer, Kfar Saba (IL); Omry Ben Ezra, Tel-Aviv (IL)

(73) Assignee: GAUZY LTD., Tel Aviv (IL)

( * ) Notice: Subject to any disclaimer, the term of this patent is extended or adjusted under 35 U.S.C. 154(b) by 551 days.

(21) Appl. No.: 16/301,077

(22) PCT Filed: May 10, 2017

(86) PCT No.: PCT/IL2017/050516
§ 371 (c)(1),
(2) Date: Nov. 13, 2018

(87) PCT Pub. No.: WO2017/195200
PCT Pub. Date: Nov. 16, 2017

(65) Prior Publication Data
US 2021/0271124 A1    Sep. 2, 2021

Related U.S. Application Data

(60) Provisional application No. 62/333,841, filed on May 10, 2016.

(51) Int. Cl.
*A61M 21/00*   (2006.01)
*G02F 1/133*   (2006.01)
*B60J 3/04*    (2006.01)
*B60J 1/20*    (2006.01)

(52) U.S. Cl.
CPC ............ *G02F 1/13306* (2013.01); *B60J 1/20* (2013.01); *B60J 3/04* (2013.01)

(58) Field of Classification Search
CPC .................................................... G02C 5/001
See application file for complete search history.

(56) References Cited

U.S. PATENT DOCUMENTS

| 5,966,680 A | 10/1999 | Butnaru |
| 6,932,090 B1* | 8/2005 | Reschke ............... A61M 21/00 128/897 |
| 8,718,796 B2* | 5/2014 | Cevette ................ A61N 1/3603 607/148 |

(Continued)

FOREIGN PATENT DOCUMENTS

CN    201304883    9/2009

*Primary Examiner* — Sang V Nguyen
(74) *Attorney, Agent, or Firm* — Duane Morris LLP; Gregory M. Lefkowitz

(57) ABSTRACT

A system to prevent motion sickness to at least one passenger in a moving vehicle, comprising: at least one liquid crystal film; at least one power dimmer apparatus operative to provide AC current to said at least one liquid crystal film; at least one sensor operative to sense the motion of said vehicle; at least one non-transitory computer-readable medium for producing a signal for activating and deactivating said at least one liquid crystal film in a certain frequency by means of said at least one power dimmer apparatus; wherein said activating and deactivating said at least one liquid crystal film is done in form of visual cues directly coordinated by motion sensory inputs provided by said at least one sensor.

16 Claims, 13 Drawing Sheets

(56) References Cited

U.S. PATENT DOCUMENTS

| | | |
|---|---|---|
| 2008/0036187 A1 | 2/2008 | Breed |
| 2009/0179987 A1 | 7/2009 | Kim |
| 2010/0161177 A1* | 6/2010 | Yuter .......................... B60J 3/02 701/36 |
| 2015/0120149 A1 | 4/2015 | Worrel et al. |
| 2016/0077345 A1 | 3/2016 | Bohan et al. |

* cited by examiner

MOTION SICKNESS ASSESSMENT QUESTIONNAIRE (MSAQ).

*Instructions.* Using the scale below, please rate how accurately the following statements describe your experience Not at all                                                      Severely

1——2——3——4——5——6——7——8——9

1. I felt sick to my stomach (G)
2. I felt faint-like (C)
3. I felt annoyed/irritated (S)
4. I felt sweaty (P)
5. I felt queasy (G)
6. I felt lightheaded (C)
7. I felt drowsy (S)
8. I felt clammy/cold sweat (P)
9. I felt disoriented (C)
10. I felt tired/fatigued (S)
11. I felt nauseated (G)
12. I felt hot/warm (P)
13. I felt dizzy (C)
14. I felt like I was spinning (C)
15. I felt as if I may vomit (G)
16. I felt uneasy (S)

*Note.* G; Gastrointestinal; C: Central; P: Peripheral; SR; Sopite-related.

Figure 13

ADVANCED LIQUID CRYSTAL FILM FOR ANTI MOTION SICKNESS AND METHODS THEREOF

CROSS-REFERENCE TO RELATED APPLICATIONS

This application is a § 371 national stage entry of International Application No. PCT/IL2017/050516, filed May 10, 2016, which claims priority to U.S. Patent Application No. 62/333,841, filed May 10, 2016, the entire contents of which are incorporated herein by reference.

TECHNICAL FIELD

The present invention relates to systems and methods comprising liquid crystal displays and specifically to systems and methods comprising liquid crystal displays for use as motion sickness management systems.

BACKGROUND

Motion sickness is a well-known malady that often occurs due to exposure to motion in the environment. Motion sickness is likely to occur on boats subject to rolling motion, car travel, train travel, and the like. The symptoms may include vertigo or nausea. There is a wide variation between different individuals in sensitivity to motion sickness. Moreover, for those persons affected, the symptoms can range from quite severe to minimal. There are various prior art theories as to the cause of motion sickness. Some of these theories are discussed hereinafter.

Traditional treatment for motion sickness has relied substantially on two primary methods: (1) adaptation, wherein individuals are repeatedly exposed to a motion environment known to induce sickness, or (2) drugs used to prevent the development of symptoms. Both methods have significant problems.

The adaptation method requires weeks (or even months) of exposure time to the provocative environment. Even after treatment, the individual may only be resistant to motion in that specific environment. While the use of drugs for the treatment of motion sickness have significant side effects, e.g., drowsiness. Drugs can only be used in situations where these side effects are not a factor. In addition, various other remedies are often proposed. For instance, medications and devices are available off-the-shelf. Some of these remedies are questionable in their treatment ability (meaning that there are no scientific empirical tests that demonstrate how well these products may work when compared against a placebo, nor what their effect may be in different motion environments).

Research performed by Bles et. al. reviewed the various forms of motion sickness, and redefined the classic sensory rearrangement theory by demonstrating that only one type of conflict is necessary and sufficient to explain all different kinds of motion sickness. They provide a mathematical description from the summarizing statement that "All situations which provoke motion sickness are characterized by a condition in which the sensed vertical as determined on the basis of integrated information from the eyes, the vestibular system and the non-vestibular proprioceptors is at variance with subjective vertical as expected from previous experience".

Furthermore, research performed more than 20 years ago to investigate adaptation was conducted by having the subjects wear prism glasses that reversed vision in the horizontal plane (Jones and Mandl, 1981). It was discovered that when wearing these left-right reversing prisms many subjects would develop symptoms like those of motion sickness. Due to the variation in persons and motion environments, it was not clear if these symptoms would be replicable in actual motion environments. In one aspect of this testing, it was found that the symptoms were avoided if the visual surroundings were illuminated with a brief stroboscopic flash designed to provide a 3 μsec view of the visual scene. The flashes were kept brief to avoid any slip of an image on the retina, which is theorized to be related to motion sickness. It was also found that adaptation occurred during stroboscopic illumination, suggesting that mechanisms other than retinal slip may be involved in adapting to changes in the vestibular system. While the results were of interest, the use of stroboscopic flashes, except in the laboratory environment, does not provide a means for controlling motion sickness, even assuming the results are extended to motion environments.

Manufacturers presently sell LCD shutter glasses wherein the two lenses each operate independently, typically alternately, in order to produce a stereoscopic effect when viewing a computer screen. However, such LCD shutter glasses cannot be utilized to prevent motion sickness, and in some cases, have been found to cause discomfort especially when used for extended durations.

Various theories and devices intended for prevention of motion sickness are shown in the following patents.

U.S. Pat. No. 6,866,225B2, published on 15 Mar. 2005, to The Boeing Company, disclose methods and systems for presenting images to vehicle occupants. A system in accordance with one embodiment of the invention includes at least one display portion configured to display an image and be positioned proximate to a seat location within the vehicle. A first signal receiving portion can be configured to receive an input image signal, and a second signal receiving portion can be configured to receive a motion signal corresponding to a motion of the vehicle. A processing portion can be configured to direct to the at least one display portion a time-varying output signal that appears to move by less than an object actually positioned external to the vehicle would appear to move to an occupant at the seat location of the vehicle. Accordingly, the viewer may be less susceptible to motion sickness by receiving visual cues that correspond to less motion than the occupant feels.

U.S. Pat. No. 8,690,750B2, published on 8 Apr. 2014, to Wesley W. O. Krueger, disclose an improved system and method to provide a human user with symbology to ameliorate, prevent or shorten the duration of disorientation or motion sickness effects caused by spatial disorientation by using a head-attachable unit.

U.S. Pat. No. 8,708,884B1, published on 29 Apr. 2014, to The United States Of America as Represented by The Secretary Of The Army, disclose methods and apparatus for adaptively mitigating motion sickness in an operator. In some embodiments, a compensatory modulator for use with a display controller included in a system to adaptively mitigating motion sickness in an operator may include one or more inputs to receive at least one of physiological measurements of the operator or operator activity behavior from one or more monitoring devices, and a motion sickness expert system configured to (a) determine a cognitive state of the operator based on the received inputs, (b) compute mitigating display parameters based on the determined cognitive state of the operator, (c) output the computed mitigating display parameters to the display controller.

U.S. Pat. No. 9,153,009B2, published on 6 Oct. 2015, to Samuel Kim, disclose a motion sickness reduction device which includes an image capture device for capturing an image device environment and an image display device for displaying image related to the captured image. In order to effectively prevent or reduce motion sickness, the right amount of motion must be displayed on the image display device when the vehicle accelerates or turns. Various methods are disclosed for adjusting the image on the display device and/or the angle of the environment subtended to make the motion sickness reduction device effective.

Finally and most relevant, U.S. Pat. No. 6,932,090B1, published on 23 Aug. 2005 to The United States Of America as Represented by The United States National Aeronautics and Space Administration (NASA), disclose methods and apparatus for treating motion sickness. The method of the invention comprises operating eyewear having shutter lenses to open said shutter lenses at a selected operating frequency ranging from within about 3 Hz to about 50 Hz. The shutter lenses are opened for a short duration at the selected operating frequency wherein the duration is selected to prevent retinal slip. The shutter lenses may be operated at a relatively slow frequency of about 4 Hz when the user is in passive activity such as riding in a boat or car or in limited motion situations in a spacecraft. The shutter lenses may be operated at faster frequencies related to motion of the user's head when the user is active.

All aforementioned disclosures are intended for, and some use very complex systems that are not suitable for all types of vehicles. Therefore, there is still a long felt need for a system and methods for managing, reducing and/or avoiding motion sickness.

The above described prior art does not show the solution provided by the present invention. As taught by the present invention, it would be desirable to provide a system that can be used without training and for more than one user at a time. It would be desirable that the system will not be a wearable system. It would be desirable that the system be useable in every environment where motion sickness may be a factor including all types of environments. It would be desirable that this system results in very minimal or no side effects for practically everyone. It would be desirable that the system will be imperceptible when it is not activated or used. It would be desirable that the system permit an operator to operate equipment including planes, boats, cars, books or electronic devices.

Those skilled in the art have long sought and will appreciate the present invention that addresses these and other problems.

SUMMARY OF THE INVENTION

It is hence one object of the invention to disclose a system to prevent motion sickness to at least one passenger in a moving vehicle, comprising: at least one liquid crystal film; at least one power dimmer apparatus operative to provide AC current to said at least one liquid crystal film; at least one sensor operative to sense the motion of said vehicle; at least one non-transitory computer-readable medium for producing a signal for activating and deactivating said at least one liquid crystal film in a certain frequency by means of said at least one power dimmer apparatus; wherein said activating and deactivating said at least one liquid crystal film is done in form of visual cues directly coordinated by motion sensory inputs provided by said at least one sensor.

It is hence another object of the invention to disclose a system to prevent motion sickness to at least one passenger in a moving vehicle, comprising: at least one liquid crystal film; at least one power dimmer apparatus operative to provide AC current to said at least one liquid crystal film; at least one non-transitory computer-readable medium for producing a signal for activating and deactivating said at least one liquid crystal film by means of said at least one power dimmer apparatus, said at least one non-transitory computer-readable medium comprising instructions thereon, that when executed on a processor, perform the steps of: activating and deactivating said liquid crystal film at an operating frequency less than about 50 Hz; providing that an exposure time for each said activating has a duration less than about one-half of a period of said operating frequency.

It is hence another object of the invention to disclose a system to prevent motion sickness to at least one passenger in a moving vehicle, comprising: at least one liquid crystal film; at least one power dimmer apparatus operative to provide AC current to said at least one liquid crystal film; at least one non-transitory computer-readable medium for producing a signal for activating and deactivating said at least one liquid crystal film by means of said at least one power dimmer apparatus, said at least one non-transitory computer-readable medium comprising instructions thereon, that when executed on a processor, perform the steps of: activating and deactivating said liquid crystal film at an operating frequency less than about 50 Hz; providing that an exposure time for each said activating has a duration less than about one-half of a period of said operating frequency; at least one sensor connected to said at least one non-transitory computer-readable medium; wherein said sensor provides inputs to said at least one non-transitory computer-readable medium thereby modifying said activating and deactivating of said liquid crystal.

A further object of the invention is to disclose any of the above systems, wherein said activating of said liquid crystal film influence light transmittance through said film in any interval from about 1% to about 99% by means of said at least one power dimmer apparatus.

A further object of the invention is to disclose any of the above systems, wherein said liquid crystal film can be activated or deactivated without any frequency, thereby being used as a regular darkening device.

A further object of the invention is to disclose any of the above systems, wherein said system further comprises at least one sensor selected from group consisting of light sensor; GPS; thermometer; tilt gauge; and any combination thereof.

A further object of the invention is to disclose any of the above systems, wherein said at least one liquid crystal film is either retrofitted, mounted, attached, adhered, laminated between glasses or allocated on the windows of said vehicle.

A further object of the invention is to disclose any of the above systems, wherein said liquid crystal film partially covers the visual field of said windows.

A further object of the invention is to disclose any of the above systems, wherein said at least one liquid crystal film are the windows of said vehicle.

A further object of the invention is to disclose any of the above systems, wherein more than one of said at least one liquid crystal film can be placed in one of said windows.

A further object of the invention is to disclose any of the above systems, wherein each of said at least one liquid crystal film can be activated or deactivated independently.

A further object of the invention is to disclose any of the above systems, wherein said vehicle is selected from a group consisting of terrestrial, aquatic, aerial, and any combination thereof.

A further object of the invention is to disclose any of the above systems, wherein the duration of the exposure time is short enough to prevent retinal slip of an image through said at least one liquid crystal film with respect to a sensing surface of a user's eye.

A further object of the invention is to disclose any of the above systems, wherein said frequency is at an operating frequency from about 1 Hz to about 1000 Hz.

A further object of the invention is to disclose any of the above systems, wherein said exposure time is less than about 10 milliseconds.

A further object of the invention is to disclose any of the above systems, wherein said at least one liquid crystal film is characterized by a liquid crystal dispersion morphology in polymer matrix of nano-droplets, micro-droplets, macro-droplets or polymer network.

A further object of the invention is to disclose any of the above systems, wherein said at least one liquid crystal film is characterized by the possibility of containing dichroic organic, metal-organic and inorganic dyes.

A further object of the invention is to disclose any of the above systems, wherein said at least one liquid crystal film is characterized by the possibility of containing metallized films with static solar-reflection mode.

A further object of the invention is to disclose any of the above systems, wherein said at least one liquid crystal film is characterized by the possibility of containing broad-band cholesteric materials for dynamic solar-reflection mode.

A further object of the invention is to disclose any of the above systems, wherein said at least one liquid crystal film comprises a low-definition display or signage.

A further object of the invention is to disclose any of the above systems, wherein said at least one liquid crystal film comprises bistable capabilities.

A further object of the invention is to disclose any of the above systems, wherein the activation of the system is defined by the minimal activation of stimuli necessary to provide said subject with at least one MSAQ scale point less than the corresponding subject without activating the system under the same conditions.

It is hence another object of the invention to disclose a method of translating sensed motion of a vehicle into motion cues perceived by at least one passenger, comprising the steps of: providing: at least one liquid crystal film; at least one power dimmer apparatus operative to provide AC current to said at least one liquid crystal film; at least one sensor operative to sense the motion of said vehicle; at least one non-transitory computer-readable medium for producing a signal for activating and deactivating said at least one liquid crystal film in a certain frequency by means of said at least one power dimmer apparatus, said at least one non-transitory computer-readable medium comprising instructions thereon executed on a processor; retrofitting/mounting/attaching/adhering/laminating/allocating said at least one liquid crystal film on the surface of said vehicle; activating said non-transitory computer-readable medium to execute the following instructions while in motion: receiving motion sensory inputs from said at least one sensor; activating and deactivating said at least one liquid crystal film in the form of visual cues according to said motion sensory inputs.

It is hence another object of the invention to disclose a method of presenting at least one motion cue to at least one passenger's peripheral vision system, comprising the steps of: providing: at least one liquid crystal film; at least one power dimmer apparatus operative to provide AC current to said at least one liquid crystal film; at least one sensor operative to sense the motion of said vehicle; at least one non-transitory computer-readable medium for producing a signal for activating and deactivating said at least one liquid crystal film at a certain frequency by means of said at least one power dimmer apparatus, said at least one non-transitory computer-readable medium comprising instructions thereon executed on a processor; retrofitting/mounting/attaching/adhering/laminating/allocating said at least one liquid crystal film on the surface of said vehicle; activating said non-transitory computer-readable medium to execute the following instructions while in motion: receiving motion sensory inputs from said at least one sensor; activating and deactivating said at least one liquid crystal film in the form of visual cues according to said motion sensory inputs.

It is hence another object of the invention to disclose a method of presenting at least one motion cue to at least one passenger's peripheral vision system, comprising the steps of: providing; at least one liquid crystal film; at least one power dimmer apparatus operative to provide AC current to said at least one liquid crystal film; at least one sensor operative to sense the motion of said vehicle; at least one sensor operative to sense the directionality of the gaze of said at least one passenger; at least one non-transitory computer-readable medium for producing a signal for activating and deactivating said at least one liquid crystal film by means of said at least one power dimmer apparatus, said at least one non-transitory computer-readable medium comprising instructions thereon executed on a processor; retrofitting/mounting/attaching/adhering/laminating/allocating said at least one liquid crystal film on the surface of said vehicle; activating said non-transitory computer-readable medium to execute the following instructions while in motion: receiving motion sensory inputs from said at least one sensor; activating and deactivating said at least one liquid crystal film in the form of visual cues according to said motion sensory inputs; activating and deactivating said at least one liquid crystal film when said directionality of said gaze of said at least one passenger is not towards the window of said vehicle.

It is hence another object of the invention to disclose a method of minimizing the effect on lightning inside a vehicle due to flickering of an anti-motion sickness system, said anti-motion sickness system comprising at least one liquid crystal film; at least one power dimmer apparatus operative to provide AC current to said at least one liquid crystal film; at least one non-transitory computer-readable medium for producing a signal for activating and deactivating said at least one liquid crystal film in a certain frequency by means of said at least one power dimmer apparatus; said method comprising the steps of: providing: at least one lightning sensor; at least one non-transitory computer-readable medium; activating said non-transitory computer-readable medium to execute the following instructions while said anti-motion sickness system is active: setting the desired lightning conditions in said vehicle; modifying at least one parameter of the activation of said anti-motion sickness system, selected from the group consisting of: frequency, light transmittance through the film, voltage, contrast, transparency, phase shift, and any combination thereof; as to reach said desired lightning conditions in said vehicle.

It is hence another object of the invention to disclose a method to prevent motion sickness to at least one passenger in a moving vehicle, comprising the steps of: providing; at least one liquid crystal film being operable for partially blocking vision to at least one eye of at least one user through said at least one liquid crystal film by activating said at least one liquid crystal film, said at least one liquid crystal film being operable for simultaneously permitting vision to both eyes of at least one user through said at least one liquid crystal film by deactivating said at least one liquid crystal film; at least one power dimmer apparatus operative to provide AC current to said at least one liquid crystal film; a non-transitory computer-readable medium, comprising a processor, for producing a signal for activating and deactivating said at least one liquid crystal film by means of said at least one power dimmer apparatus; retrofitting/mounting/attaching/adhering/laminating/allocating said at least one liquid crystal film on the surface of said vehicle; activating said non-transitory computer-readable medium to execute instructions while in motion.

It is hence another object of the invention to disclose a method for treating or preventing motion sickness to at least one passenger in a moving vehicle, comprising the steps of: providing: at least one liquid crystal film being operable for providing a visual cue to said at least one passenger; at least one power dimmer apparatus operative to provide AC current to said at least one liquid crystal film; a non-transitory computer-readable medium for producing a signal for activating and deactivating said at least one liquid crystal film by means of said at least one power dimmer apparatus; retrofitting/mounting/attaching/adhering/laminating/allocating said at least one liquid crystal film on the surface of said vehicle; activating said non-transitory computer-readable medium to execute said instructions, while in motion.

It is hence another object of the invention to disclose a method for treating or preventing motion sickness to at least one passenger in a moving vehicle, comprising the steps of: providing: at least one liquid crystal film being operable for providing a visual cue to said at least one passenger; at least one power dimmer apparatus operative to provide AC current to said at least one liquid crystal film; a non-transitory computer-readable medium for producing a signal for activating and deactivating said at least one liquid crystal film by means of said at least one power dimmer apparatus; at least one video camera connected to said at least one non-transitory computer-readable medium; and said at least one non-transitory computer-readable medium further comprises facial recognition instructions thereon, that when executed on said processor, perform the steps of: locating the face and eyes of said at least one passenger; evaluating directionality of said face and said eyes; if directionality is away from window, then activate said liquid crystal film; if directionality is to the window, then deactivate said liquid crystal film; retrofitting/mounting/attaching/adhering/laminating/allocating said at least one liquid crystal film on the surface of said vehicle; activating said non-transitory computer-readable medium to execute said instructions, while in motion.

It is hence another object of the invention to disclose a method of presenting at least one motion cue to at least one passenger's peripheral vision system, comprising the steps of: providing: at least one liquid crystal film; at least one power dimmer apparatus operative to provide AC current to said at least one liquid crystal film; at least one sensor operative to sense the motion of said vehicle; at least one non-transitory computer-readable medium for producing a signal for activating and deactivating said at least one liquid crystal film at a certain frequency by means of said at least one power dimmer apparatus, said at least one non-transitory computer-readable medium comprising instructions thereon executed on a processor; retrofitting/mounting/attaching/adhering/laminating/allocating said at least one liquid crystal film on the surface of said vehicle; activating said non-transitory computer-readable medium to execute the following instructions while in motion: receiving motion sensory inputs from said at least one sensor; identifying the peripheral vision areas of said at least one passenger; activating and deactivating said at least one liquid crystal film in the form of visual cues according to said motion sensory inputs only in said peripheral vision areas of said at least one passenger.

A further object of the invention is to disclose any of the above methods, wherein said peripheral vision areas are from about 30 degrees to about 110 degrees apart from the center of the eye.

A further object of the invention is to disclose any of the above methods, further providing at least one sensor operative to sense the directionality of the gaze of said at least one passenger.

A further object of the invention is to disclose any of the above methods, wherein said step of identifying the peripheral vision areas of said at least one passenger further comprises a step of evaluating the directionality of the gaze of said at least one passenger.

A further object of the invention is to disclose any of the above methods, wherein said directionality of the gaze of said at least one passenger together with the identified peripheral vision areas determine said activating and deactivating of said at least one liquid crystal film.

A further object of the invention is to disclose any of the above methods, wherein said non-transitory computer-readable medium further comprises instructions for activating and deactivating said at least one liquid crystal film when said directionality of said gaze of said at least one passenger is not towards the window of said vehicle.

A further object of the invention is to disclose any of the above methods, wherein said step of activating of said liquid crystal film influence light transmittance through said film in any interval from about 1% to about 99% by means of said at least one power dimmer apparatus.

A further object of the invention is to disclose any of the above methods, wherein said liquid crystal film can be activated or deactivated without any frequency, thereby being used as a regular darkening device.

A further object of the invention is to disclose any of the above methods, wherein said method further comprises a step of providing at least one sensor selected from group consisting of light sensor; GPS; thermometer; tilt gauge; and any combination thereof.

A further object of the invention is to disclose any of the above methods, wherein said at least one liquid crystal film are the windows of said vehicle.

A further object of the invention is to disclose any of the above methods, wherein said vehicle is selected from a group consisting of terrestrial, aquatic, aerial, and any combination thereof.

A further object of the invention is to disclose any of the above methods, wherein the duration of the exposure time is short enough to prevent retinal slip of an image through said at least one liquid crystal film with respect to a sensing surface of a user's eye.

A further object of the invention is to disclose any of the above methods, wherein said frequency is at an operating frequency from about 1 Hz to about 1000 Hz.

A further object of the invention is to disclose any of the above methods, wherein said exposure time is less than about 10 milliseconds.

A further object of the invention is to disclose any of the above methods, wherein said at least one liquid crystal film is characterized by a liquid crystal dispersion morphology in polymer matrix of nano-droplets, micro-droplets, macro-droplets or polymer network.

A further object of the invention is to disclose any of the above methods, wherein said at least one liquid crystal film is characterized by the possibility of containing dichroic organic, metal-organic and inorganic dyes.

A further object of the invention is to disclose any of the above methods, wherein said at least one liquid crystal film is characterized by the possibility of containing metallized films with static solar-reflection mode.

A further object of the invention is to disclose any of the above methods, wherein said at least one liquid crystal film is characterized by the possibility of containing broad-band cholesteric materials for dynamic solar-reflection mode.

A further object of the invention is to disclose any of the above methods, wherein said at least one liquid crystal film comprises a low-definition display or signage.

A further object of the invention is to disclose any of the above methods, wherein said at least one liquid crystal film comprises bistable capabilities.

A further object of the invention is to disclose any of the above methods, wherein said step of activating is defined by the minimal activation of stimuli necessary to provide said subject with at least one MSAQ scale point less than the corresponding subject without activating the system under the same conditions.

BRIEF DESCRIPTION OF THE DRAWINGS

FIG. 13—showing an example of a Motion Sickness Assessment Questionnaire Scale.

DETAIL DESCRIPTION OF THE PREFERRED EMBODIMENTS

The following description is provided, so as to enable any person skilled in the art to make use of the invention and sets forth the best modes contemplated by the inventor of carrying out this invention. Various modifications, however, are adapted to remain apparent to those skilled in the art, since the generic principles of the present invention have been defined specifically to provide a system comprising a liquid crystal film adapted for treating motion sickness. Thus, a novel method for using such films has been obtained.

The term "about" refers hereinafter to about ±20% of the mentioned value.

The term "frequency" refers hereinafter to the number of occurrences of a repeating event per unit time. It can be measured in mHz ($10^{-3}$ Hz), Hz ($10^0$ Hz), kHz ($10^3$ Hz), MHz ($10^6$ Hz), GHz ($10^9$ Hz), THz ($10^{12}$ Hz), and any combination thereof.

The term "phase shift" refers hereinafter to any change that occurs in the phase of one quantity, or in the phase difference between two or more quantities in any characteristic of the system or method.

The term "sensor" refers hereinafter to any electronic component, module, or subsystem whose purpose is to detect events or changes in its environment and send the information to other electronics, such as a computer processor.

Research on the control of sensory function, has suggested that integrated information from the eyes, the vestibular system and the non-vestibular proprioceptors are involved in the occurrence of motion sickness. Specifically related to the information collected from the eyes, retinal slip may be also involved in motion sickness.

The present invention presents visual/vestibular information to the central nervous system, which is believed to be a primary factor in the development of motion sickness symptoms, together with management of different tools already present in the vehicles and all controlled by a smart central unit connected to several sensors and auxiliary devices that allow a more effective and personalized management of motion sickness.

Figure 1:
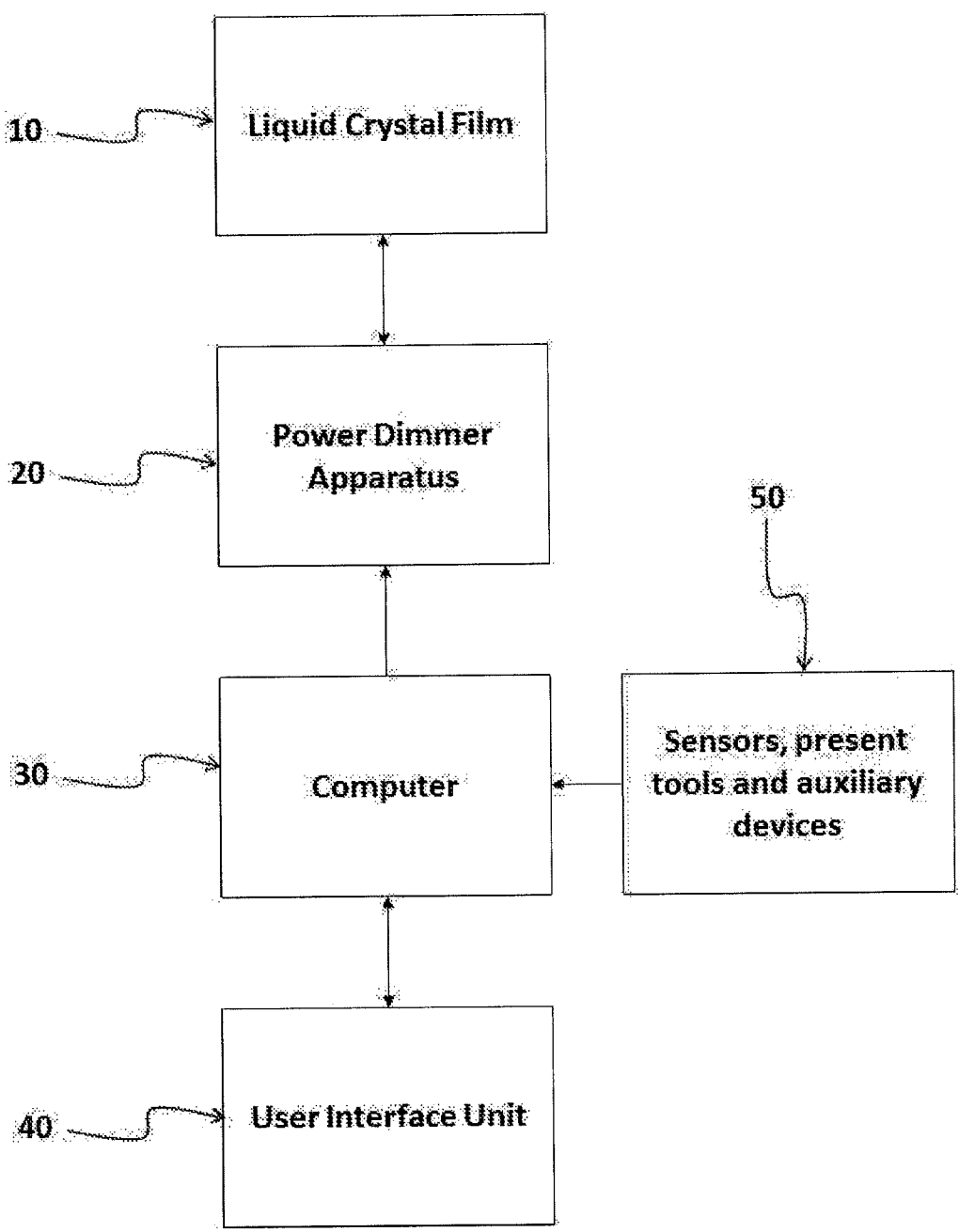
FIG. 1—showing a schematic flowchart of the components of the present invention.

Referring now to FIG. 1 showing a schematic flowchart of the components in one embodiment of the present invention. At least one liquid crystal film 10 which is retrofitted, mounted, attached, adhered, laminated between glasses or allocated on the windows of the vehicle, is directly connected to the Power Dimmer Apparatus 20 which is responsible for the activation and deactivation of the liquid crystal film. A computer 30 comprising at least one processor and a dedicated software is connected to the Power Dimmer Apparatus 20 and provides the later with the instructions on the activation and deactivation parameters. A User Interface Unit 40 in which the user can chose between different modes of activation and can chose specific personalization of said modes of activation, i.e. the frequency, the level of visibility and the time of exposure of the activation.

Lastly, connected to the computer 30, a variety of hardware 50 that provides further information which is used for the modalities of activation of the system. Examples of hardware can be divided in three main groups:

1. Already present in the vehicle: like illumination, air conditioning, entertainment systems, build-in screens, etc.
2. Sensors: like light sensor, facial-recognition camera and software, temperature sensor, etc.
3. Adjacent hardware: GPS, navigation systems (i.e. Waze™, TomTom™, Garmin™, etc.), cellphones, tablets, etc.

In several embodiments of the present invention, the computer 30 uses the information from said hardware in order to optimize the performance of the anti-motion sickness protocols. In some embodiments, the computer uses the devices present in the vehicle to facilitate the motion sickness treatment, for example control of illumination.

Any changes in the parameters of the activation of the anti-motion sickness device is characterized by a phase shift, which is any change that occurs in the phase of one quantity, or in the phase difference between two or more quantities in any of said characteristics.

Figure 2:
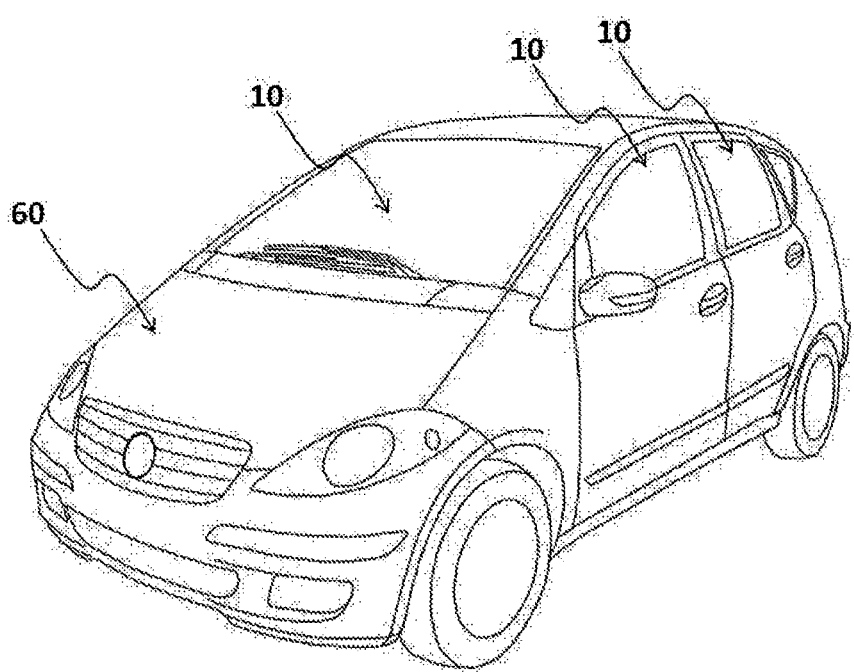
FIG. 2—showing a schematic representation of a preferred embodiment of the present invention.

Referring now to FIG. 2, showing a preferred embodiment of the present invention in which at least one fast acting, low voltage liquid crystal film 10 is placed on the windows of a car 60. However, any vehicle suitably of having windows, including boats, planes, spaceships, trains, rickshaws, etc., could be conceivably to use the present invention.

Figure 3:
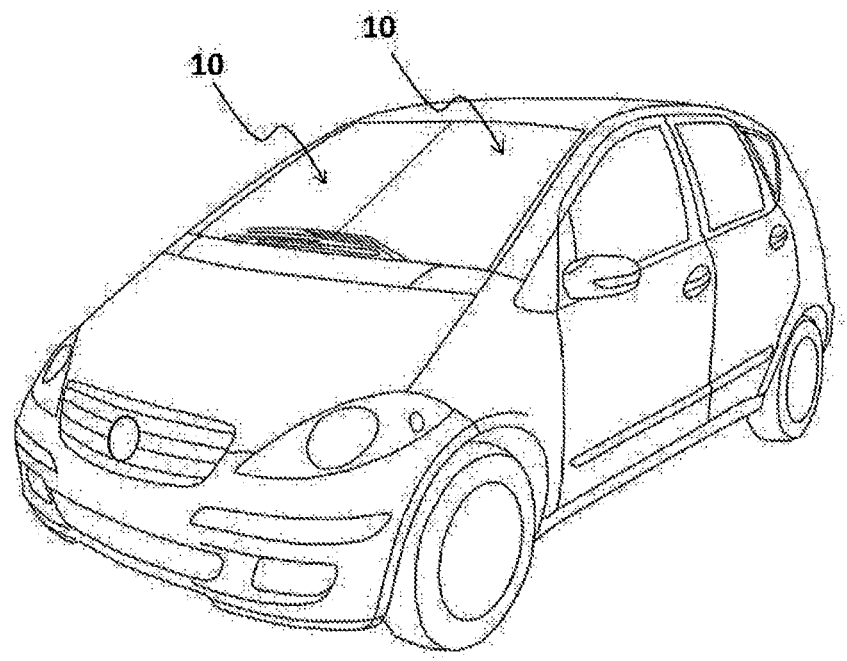
FIG. 3—showing a schematic representation of another preferred embodiment of the present invention.

Moreover, a single liquid crystal film could be utilized to cover the whole window or several independent liquid crystal films could be placed on the same window, as shown in FIG. 3, therefore dividing the action of the present invention by specific zones.

With regards with the liquid crystal films, several embodiments can be used.

Figure 4:
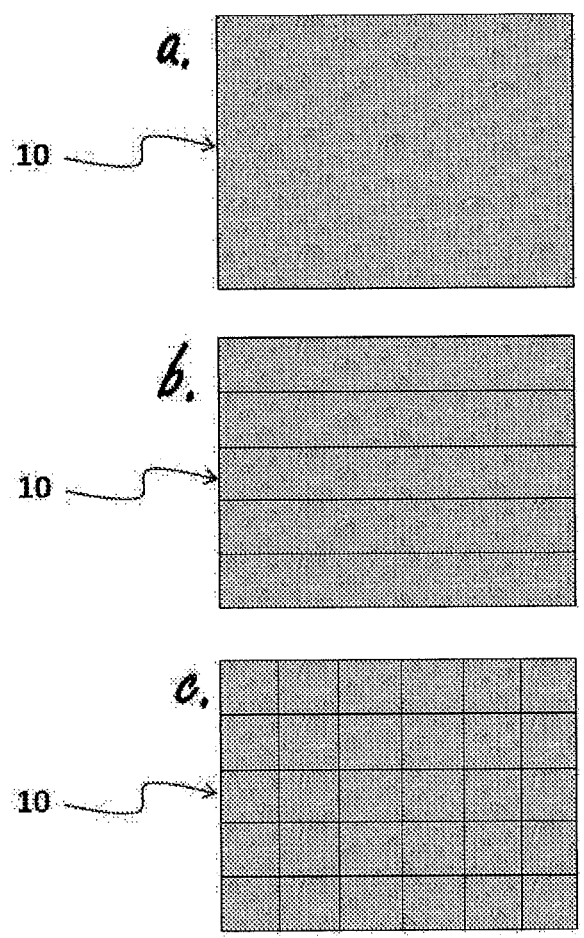
FIG. 4—showing a schematic representation of a preferred embodiment of the liquid crystal film present invention.

Referring to FIG. 4, in one embodiment, the liquid crystal film 10 can be simple (a) (one homogenous film) or complex (b-c) (stripes, pixels, etc.).

Figure 5:
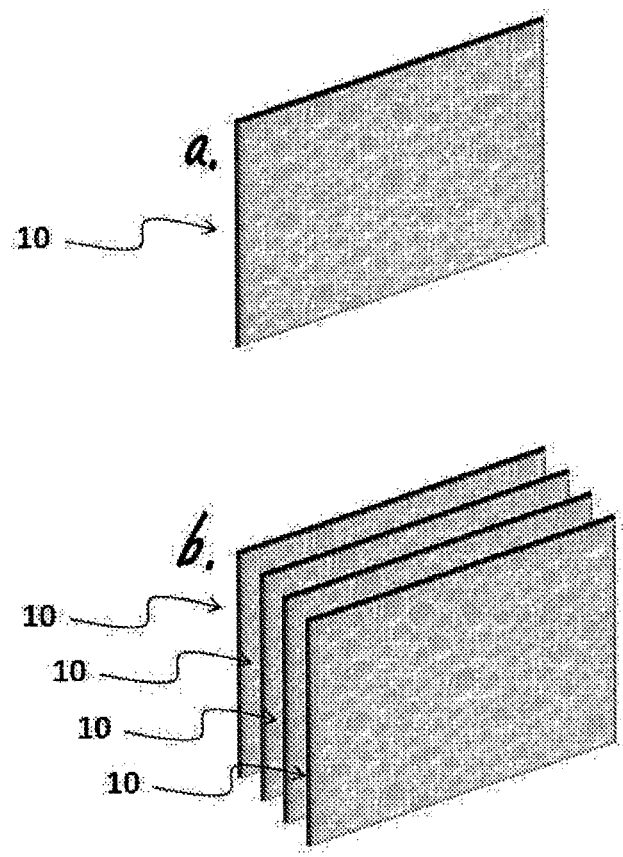
FIG. 5—showing another schematic representation of a preferred embodiment of the liquid crystal film present invention.

Referring to FIG. 5, the film can be made of a single film (a) or of several films (b).

In one embodiment, the liquid crystal film can be a solar absorbing-reflective film, comprising at least one flexible IR reflective transparent conductive film, at least one flexible transparent conductive film, at least one first layer of liquid crystal dispersions allocated between said flexible IR reflective transparent conductive film or said flexible transparent conductive film and at least one second layer of liquid crystal dispersions.

In another embodiment, the liquid crystal dispersion is made of nematic liquid crystal mixtures in said liquid crystal dispersion. The liquid crystal dispersion may comprise cholesteric liquid crystal mixtures, characterized by comprising a broad-band wavelength reflecting capabilities, in said liquid crystal dispersion adapted to reflect energy and/or chiral nematic mixtures, adapted to behave as a broadband cholesteric phase.

The liquid crystal composition can be PDLC, PNLC, PSCT or other.

The liquid crystal is characterized by a liquid crystal dispersion morphology in polymer matrix of nano-droplets, micro-droplets, macro-droplets or network gel. The liquid crystal dispersion could be made by phase separation or micro-encapsulation methods.

The liquid crystal is characterized by the possibility of containing dichroic organic and metal-organic compositions.

The liquid crystal film may comprise a pattern, a low-definition display or a signage.

The liquid crystal film may comprise bi-stable capabilities of the liquid crystal composition.

Thus, the present invention preferably comprises at least one liquid crystal film, and typically several simultaneously opening/closing liquid crystal films, depending on the number of windows, that preferably permit both eyes to simultaneously view the same scene or view or visual information.

However, it is also conceivable that the operating ranges of frequency and exposure times, as discussed hereinafter, for any of the liquid crystal films may be different. Thus, alternately or otherwise controlling activating and deactivating two different liquid crystal films 10 at the operating frequency ranges and/or exposure durations discussed herein may also be utilized to treat motion sickness. In some embodiments, the activation of different liquid crystals is synchronized, with a certain phase shift, so that when one is occluded, the opposite one may be open (and vice versa). This setting is used in order to minimize the effect of the shuttering on the overall luminance in the vehicle.

In a preferred embodiment, all liquid crystal films 10 operate simultaneously and in an identical manner with identical timing. In a preferred embodiment, liquid crystal films 10 operate as Motion sickness countermeasure. Motion sickness countermeasure 10 is preferably retrofitted, mounted, attached, adhered or allocated on the windows of the vehicle. The motion sickness countermeasure 10 can also be laminated between to glasses. The motion sickness countermeasure 10 can be used without training and in every environment where motion sickness may be a factor. Because no drugs are involved, there are virtually no side effects.

While several different environmental factors can induce motion sickness, a common factor associated with every known motion environment is the concept of sensory confusion or sensory mismatch due to variance in the integrated information from the eyes, the vestibular system and the non-vestibular proprioceptors. Motion sickness is believed to be the product of misinformation arriving at a central point, called the neural integrator, in the central nervous system. When information from the ears, joints and pressure receptors, and the visual system are all in agreement as to our orientation there is no motion sickness. However, when one or more sensory inputs to the brain is not expected, or conflicts with what is anticipated, the end product is motion sickness. Thus, it is possible to have motion sickness symptoms when the individual is at rest but the visual environment is in motion (optokinetic).

In almost every known environment that induces motion sickness, there is retinal slip (images that are normally held stationary on the sensory surface of the eye move) that is caused by a change of gain (adjustment) of the vestibular system. An intact vestibular system is necessary for motion sickness to occur. A product of the change in vestibular gain is eye movements that do not match what is expected in the central location in the brain. Prevention of retinal slip, and the prevention of sensory mismatch, will reduce the possibility for motion sickness to occur.

Thus, motion sickness countermeasure 10 works to prevent motion sickness (in all types of motion environments) by providing coherent information to the eyes, the vestibular system and the non-vestibular proprioceptors and by limiting retinal slip.

Limitation of Retinal Slip

Regarding limitation of the retinal slip, the present invention does this by limiting input to the eyes that are brief snapshots of the visual environment. The snapshots are brief enough that each snapshot freezes the image on the retina. Motion sickness countermeasure 10 does this by using liquid crystal films as electronic shutters retrofitted, mounted, attached, adhered, laminated between glasses or allocated on the windows of the vehicle. In one presently preferred embodiment, the nominal rate of strobing of the snapshots is kept low, about 3 or about 4 Hz.

Exposure time (i.e., the amount of time electronic shutters is clear) is kept short. In one presently preferred embodiment, visual exposure is provided for each snapshot about ⅓ of the period of the operational frequency. The rate of strobing may also be manually controlled, if desired. In one presently preferred embodiment, exposure time is preferably fixed but the exposure time could also be variable, selectable, and/or controllable, as desired. The exposure time is preferably set short enough to prevent retinal slippage.

In a preferred embodiment, fast response liquid crystal material is utilized in windows whose state from semi-dark to clear can be altered via abrupt changes in voltage potentials and/or changes in electric current. The reason why semi-dark is enough, is that the variation in brightness is enough to freeze the image on the cones photoreceptors while allowing to continue the vision on the rods photoreceptors. This is important for users that must continue to perform (e.g. drivers) while using the present invention.

Figure 6:
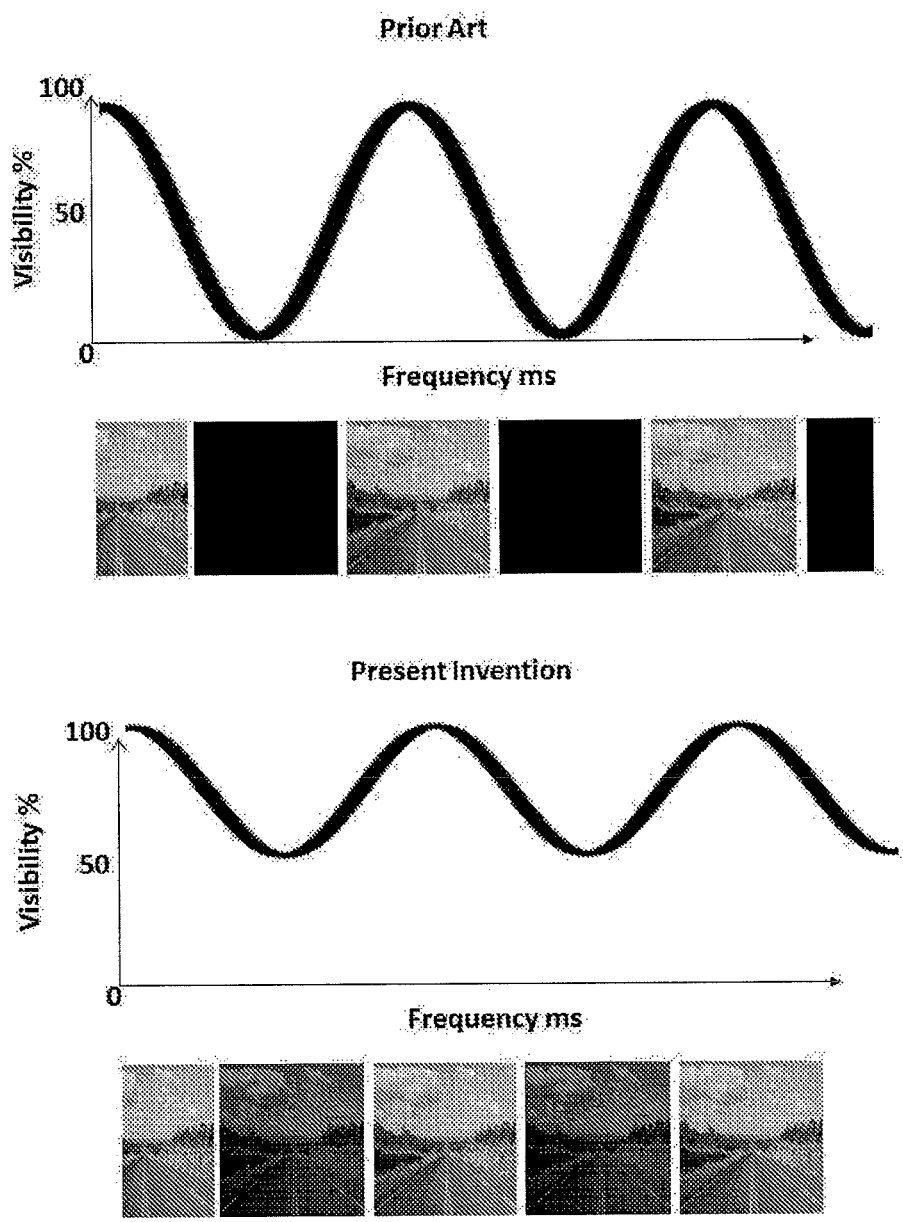
FIG. 6—showing an exemplary comparison between the prior art and the present invention regarding the relation between the frequency and the level of darkness of the liquid crystal film.

Reference now is made to FIG. 6 showing an exemplary comparison between the prior art and the present invention in regards to the relation between the frequency and the level of darkness of the liquid crystal film. The top graph shows the prior art where the flickering goes from 100% visibility to 0% visibility at a certain frequency. The bottom graph shows how the present invention works. The flickering in this example goes from 100% visibility to 50% visibility. Allowing some light to come through and be perceived by the rods photoreceptors.

It is clear that the percentage of visibility can range from 99% to 1% as necessary by the user. The level of visibility can also be tuned by the user by means of the power dimmer apparatus and the User Interface Unit.

A power dimmer apparatus operative to provide AC current is connected to the liquid crystal film. The power dimmer apparatus comprises a power switch connected in series with the film and a control circuit to achieve proper timing of turning the liquid crystal film on and off, where in order to drive the film, an output AC voltage is applied to the film, having at most a very small amount of DC voltage component. The dimmer is configured as a series connection of two anti-serially MOSFET switches and is configured as a MOSFET switch connected serially with the film through a diode bridge. The AC voltage applied to the film is of a quasi-trapezoidal form or a truncated sinusoidal form. Also, the AC voltage applied to the film has a truncated sinusoidal form which is truncated at a voltage level determined by the control circuit and applied via the power switch. In general, the maximum voltage level rating is defined for the liquid crystal film and the power dimmer apparatus has a predetermined maximum voltage level which does not exceed the liquid crystal film's maximum voltage level rating.

In one embodiment, the processor and/or software controlled computer 30 or controller device is utilized to control the power dimmer apparatus.

The frequency of operation of the power dimmer apparatus may be fixed or variable, or selectively fixed or variable, depending on the embodiment. If fixed, the frequency may preferably be about 4 Hz but preferably within the range from about 2 Hz to about 6 Hz or preferably at least in the range from about 0.5 Hz to about 10 Hz. At a frequency of about 4 Hz, many slow activity functions can be performed such as being an observer in a boat or perhaps even operating a boat under many circumstances. If the frequency is variable, a manual or automatic frequency control may be provided. If manual, then the control may be switchable or continuously variable. As activity becomes faster, then the frequency of operation may be increased. For instance, frequencies from about 25 Hz to about 50 Hz may be utilized to accommodate a user in a quick motion or faster activity operation, e.g., driving in a traffic road, although a preferred upper limit of frequency may be about 40 Hz.

As mentioned before, not only the frequency can be changed by the user, but also the level of visibility can be adjusted by the user. This allow users who have problems with night vision, and therefore have problems with their rod photoreceptors, to adjust the percentage of visibility to their needs, without losing the anti-motion sickness effects and permitting the continuation of the driving performance. Alternatively, the computer automatically chooses the contrast between open and closed sates, according to the ambient illumination. When the ambient illumination is high (such as in broad daylight), the contrast between states will be lower, and when the ambient illumination is low (such as night time), the contrast between sates is set to be higher.

In one preferred embodiment, the duration of exposure is 5 milliseconds. In any event, the exposure timing will preferably be significantly shorter than the period of operation of the liquid crystal film. Thus, in one preferred embodiment, the exposure timing is less than one-half the period of operation of the liquid crystal film but could be smaller as desired, e.g. in another embodiment the exposure timing may be at least four to five times shorter than the period of operation of the liquid crystal film The exposure timing should be in the range of values whereby the image is exposed to the retina long enough to sense the image but quickly enough so that the image does not move an appreciable amount over the retina.

In operation, the use of windows for the prevention of motion sickness is quite simple. As explained above, the liquid crystal film on the window preferably function by darkening for brief moments at a desired rate (from about 4 Hz to about 40 Hz) to permit the user to view the visual environment while simultaneously preventing image slip on the retina.

In one preferred embodiment, the liquid crystal film has three basic modes of operation as discussed subsequently. However, as explained earlier, there are many possible variations of operation.

OFF-Mode is a static mode that clears the liquid crystal film making it possible to see through the windows.

ON-Automatic Mode activates the liquid crystal films at a standard frequency of about 4 Hz and frequency adapts automatically as the speed of moving changes.

ON-Fix Mode activates the liquid crystal films at a standard frequency of about 4 Hz.

ON-Manual Mode activates the liquid crystal films at a frequency chosen by the user.

Safety of the present invention requires that their use be limited to those individuals who are not sensitive to epileptic seizures. Photosensitive epilepsy is the name given to that form of epilepsy in which seizures are provoked by flickering light that is encountered in everyday life. Photosensitive epilepsy is rather rare. About one person in every 200 is diagnosed as having epilepsy. Out of these only one person in every 10,000 has photosensitive epilepsy. The age of onset for photosensitive epilepsy is usually between 9 and 15 years. Girls are more sensitive than boys. It is rare to have onset sensitivity before the age of 5 or after the age of 20. Most individuals are aware that they suffer from this type of epilepsy and therefore, it is relatively easy to screen for those that have photosensitive epilepsy. Triggers for photosensitive epilepsy include: (1) viewing a television screen (most common), playing a video game, or computer graphics; (2) a light source that flickers at a low frequency; (3) sunlight coming through a line of trees; (4) sunlight on water; (5) looking out a train window; (6) stroboscopic lights; and (7) looking at a moving escalator. Even these triggers are not all positive for induction of photosensitive epilepsy, and require a number of other factors: (1) frequency of the light stimulation; (2) light intensity; (3) background illumination; and (4) wavelength of the light.

And usually, people with photosensitive epilepsy have had seizures both with and without flashing (flickering) light. While sensitivity varies as a function of flash frequency, it has been determined that 96% of people with photosensitive epilepsy are sensitive to light flashes from about 15 to about 20 Hz.

To reduce the possibility that motion sickness countermeasure 10 will induce photosensitive epilepsy in susceptible individuals, the basic flash rate of the liquid crystal film is preferably less than about 4 Hz (a frequency where there is little or no likelihood of inducing an epileptic episode, and taken with adherence to the following screening criteria should preclude any safety issues). Thus, those persons with this disability may use motion sickness countermeasure 10 in ON-Manual Mode, or in an embodiment which only operates as per ON-Fix Mode, which is the basic 4 Hz estimated rate. Advice of a physician should also be obtained for those persons.

Additional warnings would suggest that motion sickness countermeasure 10 should not be used by any individuals who have been diagnosed with any form of epilepsy unless under the care of a physician. Other persons who should obtain advice from a physician before use are persons' in whose family there is a history of epilepsy. Additionally, anyone who has ever had an adverse reaction of any kind to stroboscopic illumination, anyone who has ever had a neurological seizure of any kind, anyone who has ever displayed or experienced episodes of blank staring, twitching of the mouth or face, jerking movements in other parts of the body, the inability to talk or respond, or sensory hallucinations, and anyone taking any of the medications, or has ever taken any medications that are used to treat epilepsy should not use motion sickness countermeasure 10 unless under the supervision of their physician. These drugs include Carbamazepine (Tegretol, Tegretol-XR, Carbatol), Ethosuximide (Zarontin), Gabapentin (Neurontin), Lamotrigine (Lamictal) Phenobarbital, Phenytoin (Dilantin), Tiagbine (Gabitril), Topiramate (Topamax), Valproate (Depakote), and Sodium Valproate (Valproic Acid).

One advantage of the present invention is that the system can affect more than one passenger at a time, saving costs in individual personal devices. Another advantage of the present invention is that each liquid crystal film can be personalized in their action modality independently of the others. With regards of more films per window, each film can also be personalized to the needs of the different users (e.g. driver and near-driver passenger).

Providing Coherent Information to the Eyes, the Vestibular System and the Non-Vestibular Proprioceptors Research shows that the least affected person of motion sickness is usually the driver. Several reasons suggest that this is due the fact that the driver's whole mind and body are occupied with the action of driving. Initiating with the mind, the driver knows where the vehicle is going, therefore the body (non-vestibular proprioceptors) knows to prepare for the future movements of the vehicle (affecting the vestibular system). The wide-angle undisturbed vision of the driver (the eyes), provides him with the tools to understand its position in relation to the exterior, giving him a complete sense of what is happening while driving.

It is obvious that all the passengers cannot drive the vehicle. Therefore, there is need to complement the passengers with the required information regarding the current motion and the future paths of the vehicle.

Figure 7:
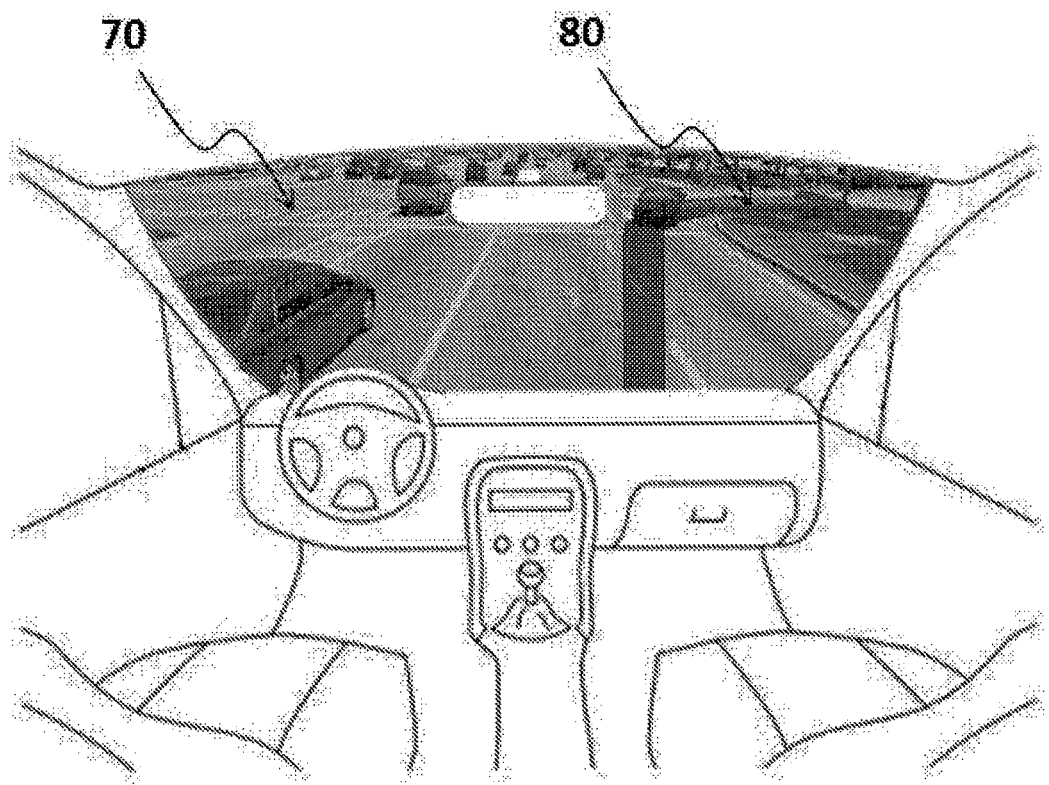
FIG. 7—showing a schematic representation of a preferred embodiment of the present invention.

The present invention provides this information in several ways:

Driving directions on the windshield/build-in screens: in the case of liquid crystal films manufactured with pixels, almost any image can be reproduced. Referring now to FIG. 7, reproduction of the driving path 80 on the front windshield 70 and/or on the build-in screens, will provide the necessary information to the passengers about the current and future movements of the vehicle.

Figure 8:
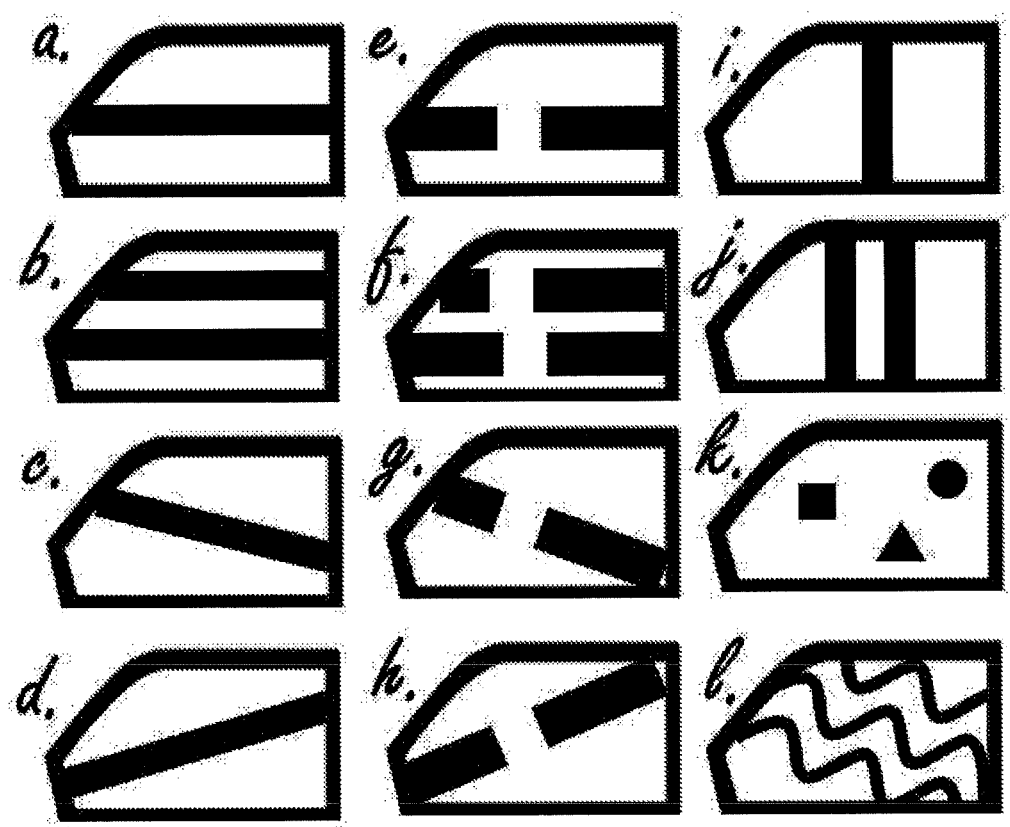
FIG. 8—showing another schematic representation of a preferred embodiment of the present invention.

Providing an artificial horizon: since in each window there is a liquid crystal film 10, an artificial horizon can be reproduced. Referring now to FIG. 8 showing different embodiments of this feature. On the left side from top to bottom, (a) a continuous fixed line is reproduced on the window. Optionally two lines (b) can be reproduced. In case the vehicle is going downhill (c) or uphill (d), the line can be reproduced in a diagonal matter. This feature can be further controlled by a digital/analog tilt gauge connected to the computer 30. In another embodiment, the line is not continuous, but is a dotted or dashed line that "runs" on the window depending on the velocity of the vehicle (e-h). In yet another embodiment, the line can be continuous vertical (i) or not-continuous vertical (j). In another embodiment, the use of geometrical forms may be used (e.g. square, circle, triangle in k.) or a variety of waves (l). It will be obvious to a person having an ordinary skill in the art, that variations of displays can be generated using the liquid crystal film, and there is no need to attempt showing them all.

In some embodiments the "artificial horizon" feature acts just as a real artificial horizon would, showing the direction of the car relative to the horizon (slanted sideways, up or down). In some embodiments the "artificial horizon" acts differently than an artificial horizon would, and shows information on where the car is accelerating to, i.e showing the vectors of force acting. In these embodiments, the artificial horizon may move even when the direction of the orientation of the car does not. For example, when accelerating down a slope, the artificial horizon might continue moving up, even if the slope is constant.

Peripheral Vision

Figure 9:
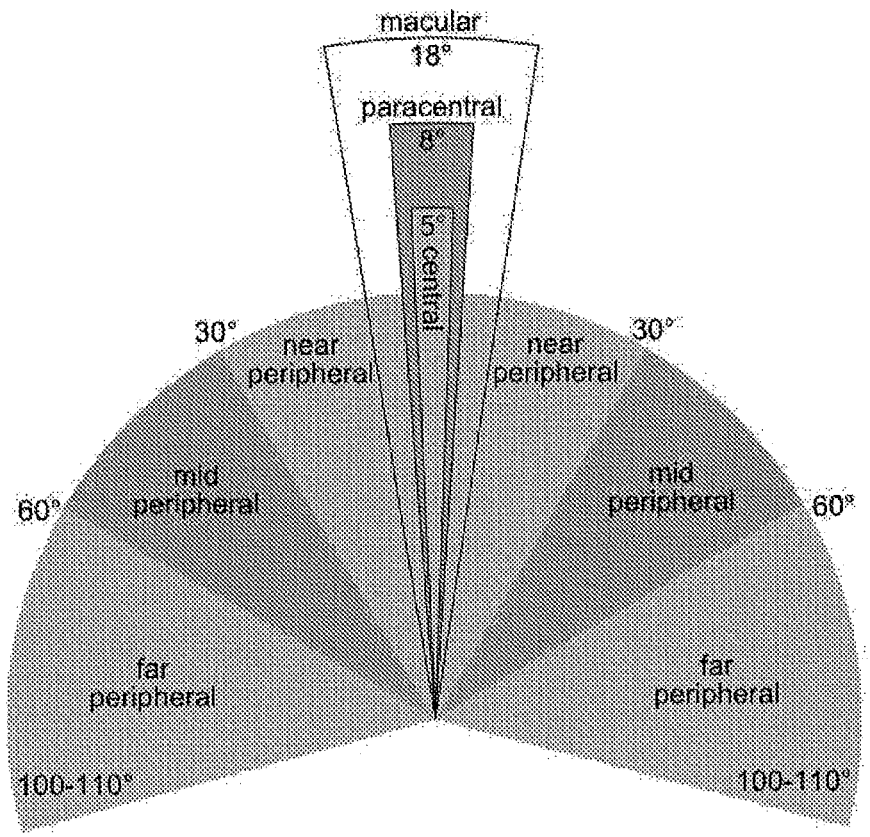
FIG. 9—showing a schematic representation of the visual zones of the human eye.

It has been extensively studied the differences between central vision and peripheral vision. FIG. 9 shows the distribution of the vision in humans (By Zyxwv99—Own work, CC BY-SA 4.0, https://commons.wikimedia.org/w/index.php?curid=37052186). Furthermore, in a study published by Stephen et. al., it was shown that both central and peripheral visual stimulation initially activates similar areas in the brain, the information from central versus peripheral fields of stimulation arrives in the higher visual areas via different routes. That is, peripheral information has access to fast, direct pathways that allow for faster onset times in dorsal stream areas. In addition, sustained activation occurred in dorsal stream areas of the brain in response to peripheral stimuli, while activation in dorsal stream structures evoked by central field stimuli subsided. This suggests that not only is the dorsal stream important for determining stimulus movement and location in space, but also monitoring peripheral stimuli in general. The results of that paper suggest that within the dorsal stream there is a timing division between information received from central and peripheral visual fields.

Using this information, the present invention discloses a novel and unique method of delivering proper stimuli (information) with regards of movement and artificial horizon to the peripheral vision of passenger. This enables the passenger to use the central vision for recreational purposes (reading a book, watching a movie, etc.) while at the same time, the system delivers information through the peripheral vision, diminishing substantially the possibility of motion sickness.

It is well known that the peripheral vision is of much lower resolution than the central vision, making presentation of information to the peripheral vision extremely challenging. The current invention describes means and methods of providing information to the peripheral vision, by means of large light effectors embedded in the windows of the vehicle (or projected on large surfaces in windowless vehicles). These visual cues are specifically designed to suite the peripheral visual system. The system uses flashes (known to reduce the threshold stimulation needed for detection and attention), large images (to accommodate for the low resolution of the peripheral system), and high contrast (going from transparent to opaque). It is a scope of the present invention to provide a system that adapts the visual cues, so that they can be meaningfully perceived by the peripheral system that is notoriously low resolution system. For this, the invention uses large simple moving shapes, with movement and flicker that increases their perception by the person in the vehicle.

Furthermore, the system is adapted to identify the peripheral vision areas of each one of the passengers. As shown in FIG. 9, those areas are from about 30 degrees to about 110 degrees apart from the center of the eye.

Figure 10:
FIG. 10—showing a schematic representation of the facial recognition of the present invention.

In one embodiment of the present invention, the system comprises a camera 90 installed inside the vehicle. The camera is connected to the computer 30, which is equipped with dedicated facial recognition software, as shown schematically in FIG. 10. The system recognizes not only the faces of the passengers 91, but also the inclination and the direction of the heads, also known as gaze. Since it is known that passengers that have access to "real horizon" suffer less of motion sickness, the system activates and deactivates the anti-motion sickness protocol depending on the direction and inclination of the head of each passenger. In some embodiments, the systems turns itself OFF when the gaze of the passenger is fixed directly at a side window. In some embodiments, the systems turns OFF only part of the system, the window corresponding to the gaze of the passenger.

In several embodiments, the system comprises at least one sensor operative to sense the directionality of the gaze of each one of the passengers. Therefore, the system is adapted to use said directionality of the gaze and the identified peripheral vision areas determine how to activate or deactivate the liquid crystal film In some embodiments, the system can activate the film in some windows and deactivate in others. Also, the system is capable to modify the way the film is activated in order to keep stimulating the peripheral vision only, by keeping the activated parts of the film in specific peripheral vision areas of each passenger.

In some embodiments, the system anticipates a motion sickness inducing car motion (such as an approaching curve), and activates the system to alleviate the anticipated motion sickness.

In some embodiments, the system anticipates a motion sickness of the passenger, depending on the gaze of the passenger, anticipating motion sickness when the gaze of the passenger is fixed on an object in the car.

In some embodiments, the system adjusts (tilts) the artificial horizon according to the sensed inclination of the passenger's head, so the artificial horizon remains parallel to the direction of gaze (and/or simulating a simple forward movement in the direction of gaze).

In some embodiments, the cabin illumination apparatus (i.e. internal light) is timed to the window flickering, and is set to offset the effect of the flicker on the cabin illumination. In these embodiments, the illumination intensity is increased when the window is shut and decreased when the window is transparent. The adaptation of the lighting in the car minimizes the "side effects" of the window flicker. The "full car flicker", that is visible to the central vision, is avoided by adapting the contrast of the window states and by manipulating the cabin lighting.

In several embodiments of the present invention the system provides stimulations only to the peripheral visual field which are invisible to the central vision, unless the head is turned directly towards the window. It is known that even if stimulations are somehow perceived indirectly by the central visual field and directly by the peripheral vision field, does not mean that the person is actively noticing said stimulations. Therefore, it is a scope of the invention to present a system that minimize the (indirect) effect on the central vision, and maximize the utilization of the peripheral vision.

EXAMPLES

In all the examples below, the system may respond to real time sensed parameters or anticipate the movements described, based on a computerized navigation system.

In cases stripes are used, the width of the stripes may vary from 3 cm to 15 cm.

The examples below describe response to relatively simple motions, for the sake of example. The actual operation of the system may incorporate one or more of the effects below, in response to one or more vector motions sensed at a particular time. Images may be superimposed on each other, or combined.

1) The car is driving forward on a straight road—accelerating: the passenger may experience a mismatch between his visual system (fixed on a book) and his proprioception systems indicating acceleration. In order to minimize this conflict, the system will show vertical stripes moving across the side windows, at an accelerating rate. The person will notice these large and possibly flickering stripes with his peripheral vision, and thus the mismatch is minimized
2) The car is driving forward on a straight road—decelerating: the passenger may experience a mismatch between his visual system (fixed on a book) and his proprioception systems indicating deceleration. In order to minimize this conflict, the system will show vertical stripes moving across the side windows, at a decreasing rate (speed). The person will notice these large and possibly flickering stripes with his peripheral vision, and thus the mismatch is minimized
3) The car is "free falling" (a sudden down slope of the road): the passenger may experience a mismatch between his visual system (fixed on a book) and his proprioception systems indicating a fall. In order to minimize this conflict, the system will show an artificial horizon that moves upwards, mimicking the view of an actual fall. The person will notice the large and possibly flickering rise of the horizon with his peripheral vision, and thus the mismatch is minimized
4) The car is "lifted" (a sudden upwards bump or slope of the road): the passenger may experience a mismatch between his visual system (fixed on a book) and his proprioception systems indicating a "jump". In order to minimize this conflict, the system will show an artificial horizon that moves downwards, mimicking the view of an actual jump. The person will notice the large and possibly flickering rise of the horizon with his peripheral vision, and thus the mismatch is minimized\

5) The car takes a sudden sideways acceleration (i.e side wind, jolt of the wheel, etc.)—the system may show a rapidly increasing shape (a triangle for example), to mimic view of an actual movement towards the corresponding window 6) Combinations—if the car is accelerating downhill, the system may choose to show accelerating horizontal stripes, that do not cover the entire height of the window. The end of the stripes will act as the artificial horizon and move upwards accordingly. Etc.

7) The car is taking a strong curve to the right—the system may choose to show vertical stripes traveling across the side windows, with the stripes on the left being more spaced from each other and traveling at a lower speed in comparison to the stripes on the right.

8) A passenger is sitting in the middle of the back seat of a vehicle, looking forward at the road. Assuming the passenger is sitting about 30 centimeters from a side window, the system activates the liquid crystal display to a maximum of root 3×30 in order to remain within the 150 degrees of the peripheral vision.

In some embodiments, the stripes described are made by a stripe of occlusion, in some embodiments the same stripes are achieved by leaving a transparent stripe, while the rest of the window is occluded (or less transparent).

Figure 11:
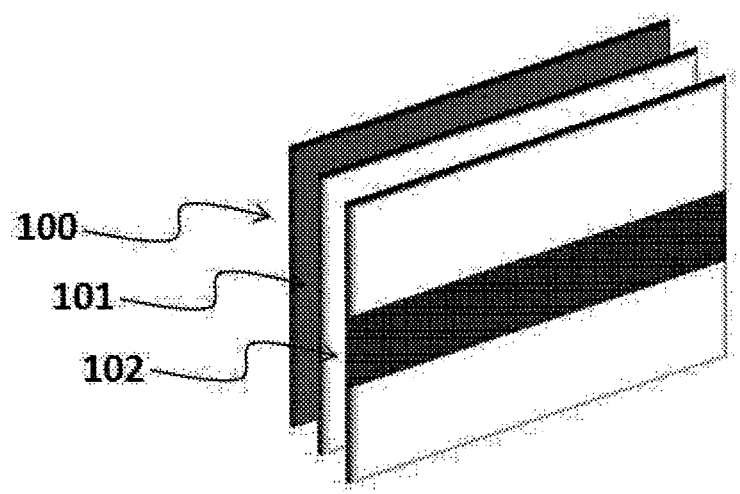
FIG. 11—showing a schematic representation of another preferred embodiment of the present invention.

Flickering of the window might disturb people outside the vehicle, like other drivers, pedestrians, etc. In another embodiment of the present invention, flickering of the window is hide by using multiple layers of films, as shown in FIG. 11. Liquid crystal film 100 is the external film that anybody from the outside will see. After liquid film 100, there will be a second liquid crystal film 101 that will have a "bright" color. Finally, the third liquid crystal film 102 will be used to provide the stimuli necessary to treat or avoid motion sickness. This organization of several liquid crystal films enables the film 102 to actuate on the bright background provided by film 101. All these stimuli are hidden from the outside world by film 100 that is dark.

Using a Well-Known Scale

Figure 12:
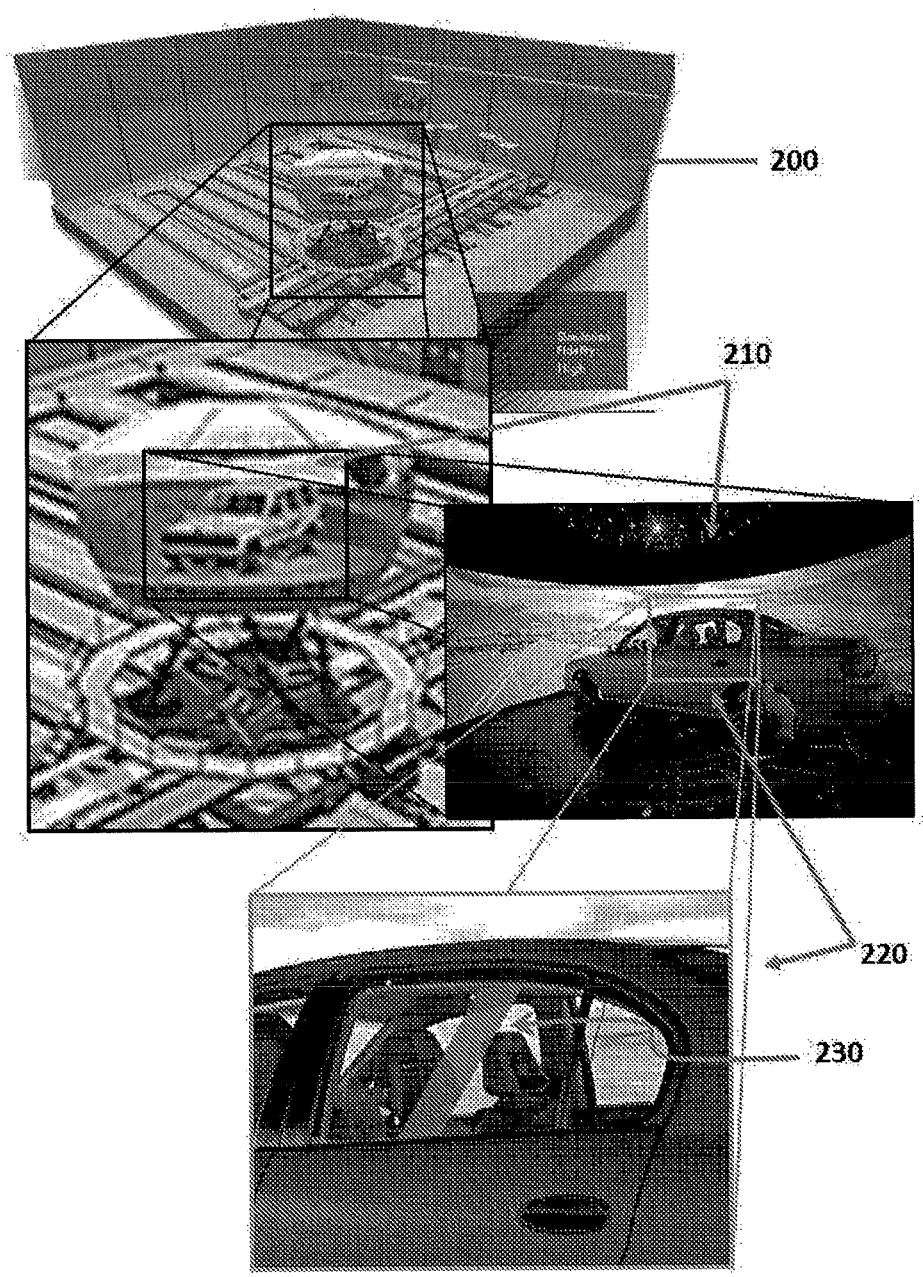
FIG. 12—showing a schematic representation of one example of experimental setup of the present invention.

In order to evaluate the efficacy of the system, motion sickness is induced in subjects using a driving simulator 200 (e.g. NADS-1 of The National Advanced Driving Simulator of the University of Iowa, https://www.nads-sc.uiowa.edu/sim_nad1.php), as shown in FIG. 12. Inside the simulator there is a full-size car 210. The car is equipped with the liquid crystal film of the invention 220, which is activated 230 (or not) during the evaluation.

The evaluation is performed using the protocols developed by Gianaros et. al. (*A Questionnaire for the Assessment of the Multiple Dimensions of Motion Sickness, Aviat Space Environ Med.* 2001 February; 72(2): 115-119), in which subjects are provided with questionnaires (Motion Sickness Assessment Questionnaire—MSAQ) for the assessment of motion sickness.

The results of the experiments are then correlated with the scale shown in FIG. 13, using the methodologies provided by the protocol.

It is well in the scope of the present invention where the system anti-motion sickness protocols/methodologies are provided in a Motion Sickness Assessment Questionnaire (MSAQ) scale.

In a preferred embodiment of the invention, each protocol/method is defined as the minimal activation of stimuli necessary to provide a subject with at least one MSAQ scale point less than the corresponding subject without activating the system under the same conditions.

In one embodiment of the present invention the system to prevent motion sickness to at least one passenger in a moving vehicle, comprises: at least one liquid crystal film; at least one power dimmer apparatus operative to provide AC current to said at least one liquid crystal film; at least one sensor operative to sense the motion of said vehicle; at least one non-transitory computer-readable medium for producing a signal for activating and deactivating said at least one liquid crystal film in a certain frequency by means of said at least one power dimmer apparatus; wherein said activating and deactivating said at least one liquid crystal film is done in form of visual cues directly coordinated by motion sensory inputs provided by said at least one sensor.

In another embodiment of the present invention the system to prevent motion sickness to at least one passenger in a moving vehicle, comprises: at least one liquid crystal film; at least one power dimmer apparatus operative to provide AC current to said at least one liquid crystal film; at least one non-transitory computer-readable medium for producing a signal for activating and deactivating said at least one liquid crystal film by means of said at least one power dimmer apparatus, said at least one non-transitory computer-readable medium comprising instructions thereon, that when executed on a processor, perform the steps of: activating and deactivating said liquid crystal film at an operating frequency less than about 50 Hz; providing that an exposure time for each said activating has a duration less than about one-half of a period of said operating frequency.

In another embodiment of the present invention the system to prevent motion sickness to at least one passenger in a moving vehicle, comprises: at least one liquid crystal film; at least one power dimmer apparatus operative to provide AC current to said at least one liquid crystal film; at least one non-transitory computer-readable medium for producing a signal for activating and deactivating said at least one liquid crystal film by means of said at least one power dimmer apparatus, said at least one non-transitory computer-readable medium comprising instructions thereon, that when executed on a processor, perform the steps of: activating and deactivating said liquid crystal film at an operating frequency less than about 50 Hz; providing that an exposure time for each said activating has a duration less than about one-half of a period of said operating frequency; at least one sensor connected to said at least one non-transitory computer-readable medium; wherein said sensor provides inputs to said at least one non-transitory computer-readable medium thereby modifying said activating and deactivating of said liquid crystal.

In several embodiments of the present invention related to the above systems, the activating of said liquid crystal film influence light transmittance through said film in any interval from about 1% to about 99% by means of said at least one power dimmer apparatus.

In several embodiments of the present invention related to the above systems, the liquid crystal film can be activated or deactivated without any frequency, thereby being used as a regular darkening device.

In several embodiments of the present invention related to the above systems, the system further comprises at least one sensor selected from group consisting of light sensor; GPS; thermometer; tilt gauge; and any combination thereof.

In several embodiments of the present invention related to the above systems, the at least one liquid crystal film is either retrofitted, mounted, attached, adhered, laminated between glasses or allocated on the windows of said vehicle.

In several embodiments of the present invention related to the above systems, the liquid crystal film partially covers the visual field of said windows.

In several embodiments of the present invention related to the above systems, the at least one liquid crystal film are the windows of said vehicle.

In several embodiments of the present invention related to the above systems, more than one of said at least one liquid crystal film can be placed in one of said windows.

In several embodiments of the present invention related to the above systems, each of said at least one liquid crystal film can be activated or deactivated independently.

In several embodiments of the present invention related to the above systems, the vehicle is selected from a group consisting of terrestrial, aquatic, aerial, and any combination thereof.

In several embodiments of the present invention related to the above systems, the duration of the exposure time is short enough to prevent retinal slip of an image through said at least one liquid crystal film with respect to a sensing surface of a user's eye.

In several embodiments of the present invention related to the above systems, the frequency is at an operating frequency from about 1 Hz to about 1000 Hz.

In several embodiments of the present invention related to the above systems, the exposure time is less than about 10 milliseconds.

In several embodiments of the present invention related to the above systems, the at least one liquid crystal film is characterized by a liquid crystal dispersion morphology in polymer matrix of nano-droplets, micro-droplets, macro-droplets or polymer network.

In several embodiments of the present invention related to the above systems, the at least one liquid crystal film is characterized by the possibility of containing dichroic organic, metal-organic and inorganic dyes.

In several embodiments of the present invention related to the above systems, the at least one liquid crystal film is characterized by the possibility of containing metallized films with static solar-reflection mode.

In several embodiments of the present invention related to the above systems, the at least one liquid crystal film is characterized by the possibility of containing broad-band cholesteric materials for dynamic solar-reflection mode.

In several embodiments of the present invention related to the above systems, the at least one liquid crystal film comprises a low-definition display or signage.

In several embodiments of the present invention related to the above systems, the at least one liquid crystal film comprises bistable capabilities.

In several embodiments of the present invention related to the above systems, the activation of the system is defined by the minimal activation of stimuli necessary to provide said subject with at least one MSAQ scale point less than the corresponding subject without activating the system under the same conditions.

In one embodiment of the present invention the method of translating sensed motion of a vehicle into motion cues perceived by at least one passenger, comprises the steps of: providing: at least one liquid crystal film; at least one power dimmer apparatus operative to provide AC current to said at least one liquid crystal film; at least one sensor operative to sense the motion of said vehicle; at least one non-transitory computer-readable medium for producing a signal for activating and deactivating said at least one liquid crystal film in a certain frequency by means of said at least one power dimmer apparatus, said at least one non-transitory computer-readable medium comprising instructions thereon executed on a processor; retrofitting/mounting/attaching/adhering/laminating/allocating said at least one liquid crystal film on the surface of said vehicle; activating said non-transitory computer-readable medium to execute the following instructions while in motion: receiving motion sensory inputs from said at least one sensor; activating and deactivating said at least one liquid crystal film in the form of visual cues according to said motion sensory inputs.

In another embodiment of the present invention the method of presenting at least one motion cue to at least one passenger's peripheral vision system, comprises the steps of: providing: at least one liquid crystal film; at least one power dimmer apparatus operative to provide AC current to said at least one liquid crystal film; at least one sensor operative to sense the motion of said vehicle; at least one non-transitory computer-readable medium for producing a signal for activating and deactivating said at least one liquid crystal film at a certain frequency by means of said at least one power dimmer apparatus, said at least one non-transitory computer-readable medium comprising instructions thereon executed on a processor; retrofitting/mounting/attaching/adhering/laminating/allocating said at least one liquid crystal film on the surface of said vehicle; activating said non-transitory computer-readable medium to execute the following instructions while in motion: receiving motion sensory inputs from said at least one sensor; activating and deactivating said at least one liquid crystal film in the form of visual cues according to said motion sensory inputs.

In another embodiment of the present invention the method of presenting at least one motion cue to at least one passenger's peripheral vision system, comprises the steps of: providing: at least one liquid crystal film; at least one power dimmer apparatus operative to provide AC current to said at least one liquid crystal film; at least one sensor operative to sense the motion of said vehicle; at least one sensor operative to sense the directionality of the gaze of said at least one passenger; at least one non-transitory computer-readable medium for producing a signal for activating and deactivating said at least one liquid crystal film by means of said at least one power dimmer apparatus, said at least one non-transitory computer-readable medium comprising instructions thereon executed on a processor; retrofitting/mounting/attaching/adhering/laminating/allocating said at least one liquid crystal film on the surface of said vehicle; activating said non-transitory computer-readable medium to execute the following instructions while in motion: receiving motion sensory inputs from said at least one sensor; activating and deactivating said at least one liquid crystal film in the form of visual cues according to said motion sensory inputs; activating and deactivating said at least one liquid crystal film when said directionality of said gaze of said at least one passenger is not towards the window of said vehicle.

In another embodiment of the present invention the method of minimizing the effect on lightning inside a vehicle due to flickering of an anti-motion sickness system, said anti-motion sickness system comprises at least one liquid crystal film; at least one power dimmer apparatus operative to provide AC current to said at least one liquid crystal film; at least one non-transitory computer-readable medium for producing a signal for activating and deactivating said at least one liquid crystal film in a certain frequency by means of said at least one power dimmer apparatus; said method comprises the steps of: providing: at least one lightning sensor; at least one non-transitory computer-readable medium; activating said non-transitory computer-readable medium to execute the following instructions while said anti-motion sickness system is active: setting the desired lightning conditions in said vehicle; modifying at least one parameter of the activation of said anti-motion sickness system, selected from the group consisting of: frequency, light transmittance through the film, voltage, contrast, transparency, phase shift, and any combination thereof; as to reach said desired lightning conditions in said vehicle.

In another embodiment of the present invention the method to prevent motion sickness to at least one passenger in a moving vehicle, comprises the steps of: providing; at least one liquid crystal film being operable for partially blocking vision to at least one eye of at least one user through said at least one liquid crystal film by activating said at least one liquid crystal film, said at least one liquid crystal film being operable for simultaneously permitting vision to both eyes of at least one user through said at least one liquid crystal film by deactivating said at least one liquid crystal film; at least one power dimmer apparatus operative to provide AC current to said at least one liquid crystal film; a non-transitory computer-readable medium, comprising a processor, for producing a signal for activating and deactivating said at least one liquid crystal film by means of said at least one power dimmer apparatus; retrofitting/mounting/attaching/adhering/laminating/allocating said at least one liquid crystal film on the surface of said vehicle; activating said non-transitory computer-readable medium to execute instructions while in motion.

In another embodiment of the present invention the method for treating or preventing motion sickness to at least one passenger in a moving vehicle, comprises the steps of: providing: at least one liquid crystal film being operable for providing a visual cue to said at least one passenger; at least one power dimmer apparatus operative to provide AC current to said at least one liquid crystal film; a non-transitory computer-readable medium for producing a signal for activating and deactivating said at least one liquid crystal film by means of said at least one power dimmer apparatus; retrofitting/mounting/attaching/adhering/laminating/allocating said at least one liquid crystal film on the surface of said vehicle; activating said non-transitory computer-readable medium to execute said instructions, while in motion.

In another embodiment of the present invention the method for treating or preventing motion sickness to at least one passenger in a moving vehicle, comprises the steps of: providing; at least one liquid crystal film being operable for providing a visual cue to said at least one passenger; at least one power dimmer apparatus operative to provide AC current to said at least one liquid crystal film; a non-transitory computer-readable medium for producing a signal for activating and deactivating said at least one liquid crystal film by means of said at least one power dimmer apparatus; at least one video camera connected to said at least one non-transitory computer-readable medium; and said at least one non-transitory computer-readable medium further comprises facial recognition instructions thereon, that when executed on said processor, perform the steps of: locating the face and eyes of said at least one passenger; evaluating directionality of said face and said eyes; if directionality is away from window, then activate said liquid crystal film; if directionality is to the window, then deactivate said liquid crystal film; retrofitting/mounting/attaching/adhering/laminating/allocating said at least one liquid crystal film on the surface of said vehicle; activating said non-transitory computer-readable medium to execute said instructions, while in motion.

In another embodiment of the present invention the method of presenting at least one motion cue to at least one passenger's peripheral vision system, comprises the steps of: providing: at least one liquid crystal film; at least one power dimmer apparatus operative to provide AC current to said at least one liquid crystal film; at least one sensor operative to sense the motion of said vehicle; at least one non-transitory computer-readable medium for producing a signal for activating and deactivating said at least one liquid crystal film at a certain frequency by means of said at least one power dimmer apparatus, said at least one non-transitory computer-readable medium comprising instructions thereon executed on a processor; retrofitting/mounting/attaching/adhering/laminating/allocating said at least one liquid crystal film on the surface of said vehicle; activating said non-transitory computer-readable medium to execute the following instructions while in motion: receiving motion sensory inputs from said at least one sensor; identifying the peripheral vision areas of said at least one passenger; activating and deactivating said at least one liquid crystal film in the form of visual cues according to said motion sensory inputs only in said peripheral vision areas of said at least one passenger.

In several embodiments of the present invention related to the above methods, the peripheral vision areas are from about 30 degrees to about 110 degrees apart from the center of the eye.

In several embodiments of the present invention related to the above methods, further providing at least one sensor operative to sense the directionality of the gaze of said at least one passenger.

In several embodiments of the present invention related to the above methods, the step of identifying the peripheral vision areas of said at least one passenger further comprises a step of evaluating the directionality of the gaze of said at least one passenger.

In several embodiments of the present invention related to the above methods, the directionality of the gaze of said at least one passenger together with the identified peripheral vision areas determine said activating and deactivating of said at least one liquid crystal film.

In several embodiments of the present invention related to the above methods, the non-transitory computer-readable medium further comprises instructions for activating and deactivating said at least one liquid crystal film when said directionality of said gaze of said at least one passenger is not towards the window of said vehicle.

In several embodiments of the present invention related to the above methods, the step of activating of said liquid crystal film influence light transmittance through said film in any interval from about 1% to about 99% by means of said at least one power dimmer apparatus.

In several embodiments of the present invention related to the above methods, the liquid crystal film can be activated or deactivated without any frequency, thereby being used as a regular darkening device.

In several embodiments of the present invention related to the above methods, the method further comprises a step of providing at least one sensor selected from group consisting of: light sensor; GPS; thermometer; tilt gauge; and any combination thereof.

In several embodiments of the present invention related to the above methods, the at least one liquid crystal film are the windows of said vehicle.

In several embodiments of the present invention related to the above methods, the vehicle is selected from a group consisting of terrestrial, aquatic, aerial, and any combination thereof.

In several embodiments of the present invention related to the above methods, the duration of the exposure time is short enough to prevent retinal slip of an image through said at least one liquid crystal film with respect to a sensing surface of a user's eye.

In several embodiments of the present invention related to the above methods, the frequency is at an operating frequency from about 1 Hz to about 1000 Hz.

In several embodiments of the present invention related to the above methods, the exposure time is less than about 10 milliseconds.

In several embodiments of the present invention related to the above methods, the at least one liquid crystal film is characterized by a liquid crystal dispersion morphology in polymer matrix of nano-droplets, micro-droplets, macro-droplets or polymer network.

In several embodiments of the present invention related to the above methods, the at least one liquid crystal film is characterized by the possibility of containing dichroic organic, metal-organic and inorganic dyes.

In several embodiments of the present invention related to the above methods, the at least one liquid crystal film is characterized by the possibility of containing metallized films with static solar-reflection mode.

In several embodiments of the present invention related to the above methods, the at least one liquid crystal film is characterized by the possibility of containing broad-band cholesteric materials for dynamic solar-reflection mode.

In several embodiments of the present invention related to the above methods, the at least one liquid crystal film comprises a low-definition display or signage.

In several embodiments of the present invention related to the above methods, the at least one liquid crystal film comprises bistable capabilities.

In several embodiments of the present invention related to the above methods, the step of activating is defined by the minimal activation of stimuli necessary to provide said subject with at least one MSAQ scale point less than the corresponding subject without activating the system under the same conditions.

In general, it will be understood that the drawings are intended to describe the concepts of the invention so that the presently preferred embodiments of the invention will be plainly disclosed to one of skill in the art but are not intended to be manufacturing level drawings or renditions of final products and may include simplified conceptual views as desired for easier and quicker understanding or explanation of the invention. As well, the relative size/type/arrangement of the components may be greatly different from that shown and still be in accord with the spirit of the invention. The processing software and/or hardware may be quite different than the disclosed presently preferred embodiments and still operate very much in accord with the invention as disclosed hereinbefore and as claimed hereinafter.

Therefore, the foregoing disclosure and description of the invention are illustrative and explanatory thereof and various changes in the method steps and also the details of the apparatus may be made within the scope of the appended claims without departing from the spirit of the invention.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

The invention claimed is:

1. A system to prevent motion sickness to at least one passenger in a moving vehicle, wherein at least one of the following is being held true:
   A. said system comprising:
      1. at least one liquid crystal film;
      2. at least one power dimmer apparatus operative to provide AC current to said at least one liquid crystal film;
      3. at least one sensor operative to sense the motion of said vehicle; and
      4. at least one non-transitory computer-readable medium for producing a signal for activating and deactivating said at least one liquid crystal film in a certain frequency by means of said at least one power dimmer apparatus;
      wherein said activating and deactivating said at least one liquid crystal film is done in form of visual cues directly coordinated by motion sensory inputs provided by said at least one sensor;
   B. said system (A), wherein at least one of the following is true:
      1. said liquid crystal film can be activated or deactivated without any frequency, thereby being used as a regular darkening device;
      2. said system further comprises at least one sensor selected from group consisting of light sensor; GPS; thermometer; tilt gauge; and any combination thereof;
      3. said at least one liquid crystal film is either retrofitted, mounted, attached, adhered, laminated between glasses or allocated on the windows of said vehicle;
      4. said at least one liquid crystal film is either retrofitted, mounted, attached, adhered, laminated between glasses or allocated on the windows of said vehicle, and said liquid crystal film partially covers the visual field of said windows; said at least one liquid crystal film are the windows of said vehicle;
      5. more than one of said at least one liquid crystal film can be placed in one of said windows;
      6. more than one of said at least one liquid crystal film can be placed in one of said windows and each of said at least one liquid crystal film can be activated or deactivated independently;
      7. said vehicle is selected from a group consisting of terrestrial, aquatic, aerial, and any combination thereof;
      8. the duration of the exposure time is short enough to prevent retinal slip of an image through said at least one liquid crystal film with respect to a sensing surface of a user's eye;
      9. said frequency is at an operating frequency from about 1 Hz to about 1000 Hz;
      10. said exposure time is less than about 10 milliseconds;
      11. said exposure time is less than about 10 milliseconds;
      12. said at least one liquid crystal film is characterized by a liquid crystal dispersion morphology in polymer matrix of nano-droplets, micro-droplets, macro-droplets or polymer network;
      13. said at least one liquid crystal film is characterized by the possibility of containing dichroic organic, metal-organic and inorganic dyes;

14. said at least one liquid crystal film is characterized by the possibility of containing metallized films with static solar-reflection mode;
15. said activating of said liquid crystal film influence light transmittance through said film in any interval from about 1% to about 99% by means of said at least one power dimmer apparatus;
16. said at least one liquid crystal film is characterized by the possibility of containing broad-band cholesteric materials for dynamic solar-reflection mode;
17. said at least one liquid crystal film comprises a low-definition display or signage;
18. said at least one liquid crystal film comprises bistable capabilities; or
19. the activation of the system is defined by the minimal activation of stimuli necessary to provide said subject with at least one MSAQ scale point less than the corresponding subject without activating the system under the same conditions;

C. said system to prevent motion sickness to at least one passenger in a moving vehicle, comprising:
  1. at least one liquid crystal film;
  2. at least one power dimmer apparatus operative to provide AC current to said at least one liquid crystal film;
  3. at least one non-transitory computer-readable medium for producing a signal for activating and deactivating said at least one liquid crystal film by means of said at least one power dimmer apparatus, said at least one non-transitory computer-readable medium comprising instructions thereon, that when executed on a processor, perform the steps of:
    i. activating and deactivating said liquid crystal film at an operating frequency less than about 50 Hz; and
    ii. providing that an exposure time for each said activating has a duration less than about one-half of a period of said operating frequency;

D. said system (C), wherein at least one of the following is true:
  1. said activating of said liquid crystal film influence light transmittance through said film in any interval from about 1% to about 99% by means of said at least one power dimmer apparatus;
  2. said liquid crystal film can be activated or deactivated without any frequency, thereby being used as a regular darkening device;
  3. said system further comprises at least one sensor selected from group consisting of light sensor; GPS; thermometer; tilt gauge; and any combination thereof;
  4. said at least one liquid crystal film is either retrofitted, mounted, attached, adhered, laminated between glasses or allocated on the windows of said vehicle;
  5. said at least one liquid crystal film is either retrofitted, mounted, attached, adhered, laminated between glasses or allocated on the windows of said vehicle and said liquid crystal film partially covers the visual field of said windows;
  6. said at least one liquid crystal film are the windows of said vehicle;
  7. more than one of said at least one liquid crystal film can be placed in one of said windows;
  8. each of said at least one liquid crystal film can be activated or deactivated independently;
  9. said vehicle is selected from a group consisting of terrestrial, aquatic, aerial, and any combination thereof;
  10. said duration of said exposure time is short enough to prevent retinal slip of an image through said at least one liquid crystal film with respect to a sensing surface of a user's eye;
  11. said operating frequency is fixed at an operating frequency less than about 10 Hz;
  12. said exposure time is less than about 10 milliseconds;
  13. said at least one liquid crystal film is characterized by a liquid crystal dispersion morphology in polymer matrix of nano-droplets, micro-droplets, macro-droplets or polymer network;
  14. said at least one liquid crystal film is characterized by the possibility of containing dichroic organic, metal-organic and inorganic dyes;
  15. said at least one liquid crystal film is characterized by the possibility of containing metallized films with static solar-reflection mode;
  16. said at least one liquid crystal film is characterized by the possibility of containing broad-band cholesteric materials for dynamic solar-reflection mode;
  17. said at least one liquid crystal film comprises a low-definition display or signage;
  18. said at least one liquid crystal film comprises bistable capabilities; or
  19. the activation of the system is defined by the minimal activation of stimuli necessary to provide said subject with at least one MSAQ scale point less than the corresponding subject without activating the system under the same conditions;

E. said system, comprising:
  1. at least one liquid crystal film;
  2. at least one power dimmer apparatus operative to provide AC current to said at least one liquid crystal film;
  3. at least one non-transitory computer-readable medium for producing a signal for activating and deactivating said at least one liquid crystal film by means of said at least one power dimmer apparatus, said at least one non-transitory computer-readable medium comprising instructions thereon, that when executed on a processor, perform the steps of:
    i. activating and deactivating said liquid crystal film at an operating frequency less than about 50 Hz; and
    ii. providing that an exposure time for each said activating has a duration less than about one-half of a period of said operating frequency; and
  4. at least one sensor connected to said at least one non-transitory computer-readable medium;
    wherein said sensor provides inputs to said at least one non-transitory computer-readable medium thereby modifying said activating and deactivating of said liquid crystal; or F. said system (E), wherein at least one of the following is true:
  1. said activating of said liquid crystal film influence light transmittance through said film in any interval from about 1% to about 99% by means of said at least one power dimmer apparatus;
  2. liquid crystal film can be activated or deactivated without any frequency, thereby being used as a regular darkening device;

3. said system further comprises at least one sensor selected from group consisting of light sensor; GPS; thermometer; tilt gauge; and any combination thereof;
4. said at least one liquid crystal film is either retrofitted, mounted, attached, adhered, laminated between glasses or allocated on the windows of said vehicle;
5. said liquid crystal film partially covers the visual field of said windows;
6. said at least one liquid crystal film are the windows of said vehicle;
7. more than one of said at least one liquid crystal film can be placed in one of said windows;
8. each of said at least one liquid crystal film can be activated or deactivated independently;
9. said vehicle is selected from a group consisting of terrestrial, aquatic, aerial, and any combination thereof;
10. said duration of said exposure time is short enough to prevent retinal slip of an image through said at least one liquid crystal film with respect to a sensing surface of a user's eye;
11. said operating frequency is fixed at an operating frequency less than about 10 Hz;
12. said exposure time is less than about 10 milliseconds;
13. said at least one liquid crystal film is characterized by a liquid crystal dispersion morphology in polymer matrix of nano-droplets, micro-droplets, macro-droplets or polymer network;
14. said at least one liquid crystal film is characterized by the possibility of containing dichroic organic, metal-organic and inorganic dyes;
15. said at least one liquid crystal film is characterized by the possibility of containing metallized films with static solar-reflection mode;
16. said at least one liquid crystal film is characterized by the possibility of containing broad-band cholesteric materials for dynamic solar-reflection mode;
17. said at least one liquid crystal film comprises a low-definition display or signage;
18. said at least one liquid crystal film comprises bistable capabilities; or
19. the activation of the system is defined by the minimal activation of stimuli necessary to provide said subject with at least one MSAQ scale point less than the corresponding subject without activating the system under the same conditions.

2. The system of claim 1, wherein A. said system comprises:
1. at least one liquid crystal film;
2. at least one power dimmer apparatus operative to provide AC current to said at least one liquid crystal film;
3. at least one sensor operative to sense the motion of said vehicle; and
4. at least one non-transitory computer-readable medium for producing a signal for activating and deactivating said at least one liquid crystal film in a certain frequency by means of said at least one power dimmer apparatus;
wherein said activating and deactivating said at least one liquid crystal film is done in form of visual cues directly coordinated by motion sensory inputs provided by said at least one sensor.

3. The system of claim 2, wherein at least one of the following is true:

1. said liquid crystal film can be activated or deactivated without any frequency, thereby being used as a regular darkening device;
2. said system further comprises at least one sensor selected from group consisting of light sensor; GPS; thermometer; tilt gauge; and any combination thereof;
3. said at least one liquid crystal film is either retrofitted, mounted, attached, adhered, laminated between glasses or allocated on the windows of said vehicle;
4. said at least one liquid crystal film is either retrofitted, mounted, attached, adhered, laminated between glasses or allocated on the windows of said vehicle, and said liquid crystal film partially covers the visual field of said windows; said at least one liquid crystal film are the windows of said vehicle;
5. more than one of said at least one liquid crystal film can be placed in one of said windows;
6. more than one of said at least one liquid crystal film can be placed in one of said windows and each of said at least one liquid crystal film can be activated or deactivated independently;
7. said vehicle is selected from a group consisting of terrestrial, aquatic, aerial, and any combination thereof;
8. the duration of the exposure time is short enough to prevent retinal slip of an image through said at least one liquid crystal film with respect to a sensing surface of a user's eye;
9. said frequency is at an operating frequency from about 1 Hz to about 1000 Hz;
10. said exposure time is less than about 10 milliseconds;
11. said exposure time is less than about 10 milliseconds;
12. said at least one liquid crystal film is characterized by a liquid crystal dispersion morphology in polymer matrix of nano-droplets, micro-droplets, macro-droplets or polymer network;
13. said at least one liquid crystal film is characterized by the possibility of containing dichroic organic, metal-organic and inorganic dyes;
14. said at least one liquid crystal film is characterized by the possibility of containing metallized films with static solar-reflection mode;
15. said activating of said liquid crystal film influence light transmittance through said film in any interval from about 1% to about 99% by means of said at least one power dimmer apparatus;
16. said at least one liquid crystal film is characterized by the possibility of containing broad-band cholesteric materials for dynamic solar-reflection mode;
17. said at least one liquid crystal film comprises a low-definition display or signage;
18. said at least one liquid crystal film comprises bistable capabilities; or
19. the activation of the system is defined by the minimal activation of stimuli necessary to provide said subject with at least one MSAQ scale point less than the corresponding subject without activating the system under the same conditions.

4. The system of claim 1, wherein C. said system to prevent motion sickness to at least one passenger in a moving vehicle, comprises:
1. at least one liquid crystal film;
2. at least one power dimmer apparatus operative to provide AC current to said at least one liquid crystal film;
3. at least one non-transitory computer-readable medium for producing a signal for activating and deactivating said at least one liquid crystal film by means of said at least one power dimmer apparatus, said at least one non-transitory computer-readable medium comprising instructions thereon, that when executed on a processor, perform the steps of:
   i. activating and deactivating said liquid crystal film at an operating frequency less than about 50 Hz; and
   ii. providing that an exposure time for each said activating has a duration less than about one-half of a period of said operating frequency.

5. The system of claim 4, wherein at least one of the following is being held true:
   1. said activating of said liquid crystal film influence light transmittance through said film in any interval from about 1% to about 99% by means of said at least one power dimmer apparatus;
   2. said liquid crystal film can be activated or deactivated without any frequency, thereby being used as a regular darkening device;
   3. said system further comprises at least one sensor selected from group consisting of light sensor; GPS; thermometer; tilt gauge; and any combination thereof;
   4. said at least one liquid crystal film is either retrofitted, mounted, attached, adhered, laminated between glasses or allocated on the windows of said vehicle;
   5. said at least one liquid crystal film is either retrofitted, mounted, attached, adhered, laminated between glasses or allocated on the windows of said vehicle and said liquid crystal film partially covers the visual field of said windows;
   6. said at least one liquid crystal film are the windows of said vehicle;
   7. more than one of said at least one liquid crystal film can be placed in one of said windows;
   8. each of said at least one liquid crystal film can be activated or deactivated independently;
   9. said vehicle is selected from a group consisting of terrestrial, aquatic, aerial, and any combination thereof;
   10. said duration of said exposure time is short enough to prevent retinal slip of an image through said at least one liquid crystal film with respect to a sensing surface of a user's eye;
   11. said operating frequency is fixed at an operating frequency less than about 10 Hz;
   12. said exposure time is less than about 10 milliseconds;
   13. said at least one liquid crystal film is characterized by a liquid crystal dispersion morphology in polymer matrix of nano-droplets, micro-droplets, macro-droplets or polymer network;
   14. said at least one liquid crystal film is characterized by the possibility of containing dichroic organic, metal-organic and inorganic dyes;
   15. said at least one liquid crystal film is characterized by the possibility of containing metallized films with static solar-reflection mode;
   16. said at least one liquid crystal film is characterized by the possibility of containing broad-band cholesteric materials for dynamic solar-reflection mode;
   17. said at least one liquid crystal film comprises a low-definition display or signage;
   18. said at least one liquid crystal film comprises bistable capabilities; or
   19. the activation of the system is defined by the minimal activation of stimuli necessary to provide said subject with at least one MSAQ scale point less than the corresponding subject without activating the system under the same conditions.

6. The system of claim 1, wherein E. said system, comprises:
   1. at least one liquid crystal film;
   2. at least one power dimmer apparatus operative to provide AC current to said at least one liquid crystal film;
   3. at least one non-transitory computer-readable medium for producing a signal for activating and deactivating said at least one liquid crystal film by means of said at least one power dimmer apparatus, said at least one non-transitory computer-readable medium comprising instructions thereon, that when executed on a processor, perform the steps of:
      i. activating and deactivating said liquid crystal film at an operating frequency less than about 50 Hz; and
      ii. providing that an exposure time for each said activating has a duration less than about one-half of a period of said operating frequency; and
   4. at least one sensor connected to said at least one non-transitory computer-readable medium;
   wherein said sensor provides inputs to said at least one non-transitory computer-readable medium thereby modifying said activating and deactivating of said liquid crystal.

7. The system of claim 6, wherein at least one of the following is being held true:
   1. said activating of said liquid crystal film influence light transmittance through said film in any interval from about 1% to about 99% by means of said at least one power dimmer apparatus;
   2. liquid crystal film can be activated or deactivated without any frequency, thereby being used as a regular darkening device;
   3. said system further comprises at least one sensor selected from group consisting of light sensor; GPS; thermometer; tilt gauge; and any combination thereof;
   4. said at least one liquid crystal film is either retrofitted, mounted, attached, adhered, laminated between glasses or allocated on the windows of said vehicle;
   5. said liquid crystal film partially covers the visual field of said windows;
   6. said at least one liquid crystal film are the windows of said vehicle;
   7. more than one of said at least one liquid crystal film can be placed in one of said windows;
   8. each of said at least one liquid crystal film can be activated or deactivated independently;
   9. said vehicle is selected from a group consisting of terrestrial, aquatic, aerial, and any combination thereof;
   10. said duration of said exposure time is short enough to prevent retinal slip of an image through said at least one liquid crystal film with respect to a sensing surface of a user's eye;
   11. said operating frequency is fixed at an operating frequency less than about 10 Hz;
   12. said exposure time is less than about 10 milliseconds;
   13. said at least one liquid crystal film is characterized by a liquid crystal dispersion morphology in polymer matrix of nano-droplets, micro-droplets, macro-droplets or polymer network;
   14. said at least one liquid crystal film is characterized by the possibility of containing dichroic organic, metal-organic and inorganic dyes;
   15. said at least one liquid crystal film is characterized by the possibility of containing metallized films with static solar-reflection mode;

16. said at least one liquid crystal film is characterized by the possibility of containing broad-band cholesteric materials for dynamic solar-reflection mode;
17. said at least one liquid crystal film comprises a low-definition display or signage;
18. said at least one liquid crystal film comprises bistable capabilities; or
19. the activation of the system is defined by the minimal activation of stimuli necessary to provide said subject with at least one MSAQ scale point less than the corresponding subject without activating the system under the same conditions.

8. A method for preventing motion sickness to at least one passenger in a moving vehicle, wherein at least one of the following is true:
A. said method is provided useful by translating sensed motion of a vehicle into motion cues perceived by at least one passenger, and comprising the steps of:
   1. providing:
      i. at least one liquid crystal film;
      ii. at least one power dimmer apparatus operative to provide AC current to said at least one liquid crystal film;
      iii. at least one sensor operative to sense the motion of said vehicle; and
      iv. at least one non-transitory computer-readable medium for producing a signal for activating and deactivating said at least one liquid crystal film in a certain frequency by means of said at least one power dimmer apparatus, said at least one non-transitory computer-readable medium comprising instructions thereon executed on a processor;
   2. retrofitting/mounting/attaching/adhering/laminating/allocating said at least one liquid crystal film on the surface of said vehicle; and
   3. activating said non-transitory computer-readable medium to execute the following instructions while in motion:
      i. receiving motion sensory inputs from said at least one sensor; and
      ii. activating and deactivating said at least one liquid crystal film in the form of visual cues according to said motion sensory inputs;
B. said method (A), wherein at least one of the following is true:
   1. said step of activating of said liquid crystal film influence light transmittance through said film in any interval from about 1% to about 99% by means of said at least one power dimmer apparatus;
   2. said liquid crystal film can be activated or deactivated without any frequency, thereby being used as a regular darkening device;
   3. said method further comprises a step of providing at least one sensor selected from group consisting of light sensor; GPS; thermometer; tilt gauge; and any combination thereof;
   4. said at least one liquid crystal film are the windows of said vehicle;
   5. said vehicle is selected from a group consisting of terrestrial, aquatic, aerial, and any combination thereof;
   6. the duration of the exposure time is short enough to prevent retinal slip of an image through said at least one liquid crystal film with respect to a sensing surface of a user's eye;
   7. said frequency is at an operating frequency from about 1 Hz to about 1000 Hz;
   8. said exposure time is less than about 10 milliseconds;
   9. said at least one liquid crystal film is characterized by a liquid crystal dispersion morphology in polymer matrix of nano-droplets, micro-droplets, macro-droplets or polymer network;
   10. said at least one liquid crystal film is characterized by the possibility of containing dichroic organic, metal-organic and inorganic dyes;
   11. said at least one liquid crystal film is characterized by the possibility of containing metallized films with static solar-reflection mode;
   12. said at least one liquid crystal film is characterized by the possibility of containing broad-band cholesteric materials for dynamic solar-reflection mode;
   13. said at least one liquid crystal film comprises a low-definition display or signage;
   14. said at least one liquid crystal film comprises bistable capabilities; or
   15. said step of activating is defined by the minimal activation of stimuli necessary to provide said subject with at least one MSAQ scale point less than the corresponding subject without activating the system under the same conditions;
C. said method comprises the steps of:
   1. providing:
      i. at least one liquid crystal film;
      ii. at least one power dimmer apparatus operative to provide AC current to said at least one liquid crystal film;
      iii. at least one sensor operative to sense the motion of said vehicle; and
      iv. at least one non-transitory computer-readable medium for producing a signal for activating and deactivating said at least one liquid crystal film at a certain frequency by means of said at least one power dimmer apparatus, said at least one non-transitory computer-readable medium comprising instructions thereon executed on a processor;
   2. retrofitting/mounting/attaching/adhering/laminating/allocating said at least one liquid crystal film on the surface of said vehicle; and
   3. activating said non-transitory computer-readable medium to execute the following instructions while in motion:
      i. receiving motion sensory inputs from said at least one sensor; and
      ii. activating and deactivating said at least one liquid crystal film in the form of visual cues according to said motion sensory inputs;
D. said method (C), wherein at least one of the following is true:
   1. said step of activating of said liquid crystal film influence light transmittance through said film in any interval from about 1% to about 99% by means of said at least one power dimmer apparatus;
   2. said liquid crystal film can be activated or deactivated without any frequency, thereby being used as a regular darkening device;
   3. said method further comprises a step of providing at least one sensor selected from group consisting of light sensor; GPS; thermometer; tilt gauge; and any combination thereof;
   4. said at least one liquid crystal film are the windows of said vehicle;
   5. said vehicle is selected from a group consisting of terrestrial, aquatic, aerial, and any combination thereof;

6. the duration of the exposure time is short enough to prevent retinal slip of an image through said at least one liquid crystal film with respect to a sensing surface of a user's eye;
7. the frequency is at an operating frequency from about 1 Hz to about 1000 Hz;
8. said exposure time is less than about 10 milliseconds;
9. said at least one liquid crystal film is characterized by a liquid crystal dispersion morphology in polymer matrix of nano-droplets, micro-droplets, macro-droplets or polymer network;
10. said at least one liquid crystal film is characterized by the possibility of containing dichroic organic, metal-organic and inorganic dyes;
11. said at least one liquid crystal film is characterized by the possibility of containing metallized films with static solar-reflection mode;
12. said at least one liquid crystal film is characterized by the possibility of containing broad-band cholesteric materials for dynamic solar-reflection mode;
13. said at least one liquid crystal film comprises a low-definition display or signage;
14. said at least one liquid crystal film comprises bistable capabilities;
15. said step of activating is defined by the minimal activation of stimuli necessary to provide said subject with at least one MSAQ scale point less than the corresponding subject without activating the system under the same conditions;
16. said method further comprising step of providing at least one sensor operative to sense the directionality of the gaze of said at least one passenger; or
17. said non-transitory computer-readable medium further comprises instructions for activating and deactivating said at least one liquid crystal film when said directionality of said gaze of said at least one passenger is not towards the window of said vehicle;

E. said method is provided useful for presenting at least one motion cue to at least one passenger's peripheral vision system; said method comprising the steps of:
1. providing:
   i. at least one liquid crystal film;
   ii. at least one power dimmer apparatus operative to provide AC current to said at least one liquid crystal film;
   iii. at least one sensor operative to sense the motion of said vehicle;
   iv. at least one sensor operative to sense the directionality of the gaze of said at least one passenger; and
   v. at least one non-transitory computer-readable medium for producing a signal for activating and deactivating said at least one liquid crystal film by means of said at least one power dimmer apparatus, said at least one non-transitory computer-readable medium comprising instructions thereon executed on a processor;
2. retrofitting/mounting/attaching/adhering/laminating/allocating said at least one liquid crystal film on the surface of said vehicle; and
3. activating said non-transitory computer-readable medium to execute the following instructions while in motion:
   i. receiving motion sensory inputs from said at least one sensor;
   ii. activating and deactivating said at least one liquid crystal film in the form of visual cues according to said motion sensory inputs; and
   iii. activating and deactivating said at least one liquid crystal film when said directionality of said gaze of said at least one passenger is not towards the window of said vehicle;

F. said method (E), wherein at least one of the following is true:
1. said step of activating of said liquid crystal film influence light transmittance through said film in any interval from about 1% to about 99% by means of said at least one power dimmer apparatus;
2. said liquid crystal film can be activated or deactivated without any frequency, thereby being used as a regular darkening device;
3. said method further comprises a step of providing at least one sensor selected from group consisting of light sensor; GPS; thermometer; tilt gauge; and any combination thereof;
4. said at least one liquid crystal film are the windows of said vehicle;
5. said vehicle is selected from a group consisting of terrestrial, aquatic, aerial, and any combination thereof;
6. the duration of the exposure time is short enough to prevent retinal slip of an image through said at least one liquid crystal film with respect to a sensing surface of a user's eye;
7. said frequency is at an operating frequency from about 1 Hz to about 1000 Hz;
8. said exposure time is less than about 10 milliseconds;
9. said at least one liquid crystal film is characterized by a liquid crystal dispersion morphology in polymer matrix of nano-droplets, micro-droplets, macro-droplets or polymer network;
10. said at least one liquid crystal film is characterized by the possibility of containing dichroic organic, metal-organic and inorganic dyes;
11. said at least one liquid crystal film is characterized by the possibility of containing metallized films with static solar-reflection mode;
12. said at least one liquid crystal film is characterized by the possibility of containing broad-band cholesteric materials for dynamic solar-reflection mode;
13. said at least one liquid crystal film comprises a low-definition display or signage;
14. said at least one liquid crystal film comprises bistable capabilities; or
15. said step of activating is defined by the minimal activation of stimuli necessary to provide said subject with at least one MSAQ scale point less than the corresponding subject without activating the system under the same conditions;

G. said method is provided useful for minimizing the effect on lightning inside a vehicle due to flickering of an anti-motion sickness system, said anti-motion sickness system comprising at least one liquid crystal film; at least one power dimmer apparatus operative to provide AC current to said at least one liquid crystal film; at least one non-transitory computer-readable medium for producing a signal for activating and deactivating said at least one liquid crystal film in a certain frequency by means of said at least one power dimmer apparatus; said method comprising the steps of:

1. providing:
   i. at least one lightning sensor; and
   ii. at least one non-transitory computer-readable medium;
2. activating said non-transitory computer-readable medium to execute the following instructions while said anti-motion sickness system is active:
3. setting the desired lightning conditions in said vehicle; and
4. modifying at least one parameter of the activation of said anti-motion sickness system, selected from the group consisting of: frequency, light transmittance through the film, voltage, transparency, phase shift, and any combination thereof; as to reach said desired lightning conditions in said vehicle;

H. said method (G), wherein at least one of the following true:
   1. said method further comprising a step of connecting the internal lightning of said vehicle to said at least one non-transitory computer-readable medium; or
   2. said method further comprising a step of activating and deactivating said internal lightning of said vehicle, when said flickering is on, at the required intensity as to reach said desired lightning conditions in said vehicle;

I. said method is provided useful for preventing motion sickness to at least one passenger in a moving vehicle, comprising the steps of:
   1. providing:
      i. at least one liquid crystal film being operable for partially blocking vision to at least one eye of at least one user through said at least one liquid crystal film by activating said at least one liquid crystal film, said at least one liquid crystal film being operable for simultaneously permitting vision to both eyes of at least one user through said at least one liquid crystal film by deactivating said at least one liquid crystal film;
      ii. at least one power dimmer apparatus operative to provide AC current to said at least one liquid crystal film; and
      iii. a non-transitory computer-readable medium, comprising a processor, for producing a signal for activating and deactivating said at least one liquid crystal film by means of said at least one power dimmer apparatus;
   2. retrofitting/mounting/attaching/adhering/laminating/allocating said at least one liquid crystal film on the surface of said vehicle; and
   3. activating said non-transitory computer-readable medium to execute instructions while in motion;

J. said method (I) wherein at least one of the following is true:
   1. said instructions, when executed on said processor, perform the steps of:
      i. activating and deactivating said at least one liquid crystal film at an operating frequency less than about 50 Hz; and
      ii. providing that an exposure time for each said activating has a duration less than about one-half of a period of said operating frequency;
   2. said step of activating of said liquid crystal film influence light transmittance through said film in any interval from about 1% to about 99% by means of said at least one power dimmer apparatus;
   3. said liquid crystal film can be activated or deactivated without any frequency, thereby being used as a regular darkening device;
   4. said method further comprises a step of providing at least one sensor selected from group consisting of light sensor; GPS; thermometer; tilt gauge; and any combination thereof;
   5. said at least one liquid crystal film are the windows of said vehicle;
   6. said vehicle is selected from a group consisting of terrestrial, aquatic, aerial, and any combination thereof;
   7. said duration of said exposure time is short enough to prevent retinal slip of an image through said at least one liquid crystal film with respect to a sensing surface of a user's eye;
   8. said operating frequency is fixed at an operating frequency less than about 10 Hz;
   9. said exposure time is less than about 10 milliseconds;
   10. said at least one liquid crystal film is characterized by a liquid crystal dispersion morphology in polymer matrix of nano-droplets, micro-droplets, macro-droplets or polymer network;
   11. said at least one liquid crystal film is characterized by the possibility of containing dichroic organic, metal-organic and inorganic dyes;
   12. said at least one liquid crystal film is characterized by the possibility of containing metallized films with static solar-reflection mode;
   13. said at least one liquid crystal film is characterized by the possibility of containing broad-band cholesteric materials for dynamic solar-reflection mode;
   14. said at least one liquid crystal film comprises a low-definition display or signage;
   15. said at least one liquid crystal film comprises bistable capabilities; or
   16. said step of activating is defined by the minimal activation of stimuli necessary to provide said subject with at least one MSAQ scale point less than the corresponding subject without activating the system under the same conditions;

K. said method is for treating or preventing motion sickness to at least one passenger in a moving vehicle, comprises the steps of:
   1. providing:
      i. at least one liquid crystal film being operable for providing a visual cue to said at least one passenger;
      ii. at least one power dimmer apparatus operative to provide AC current to said at least one liquid crystal film; and
      iii. a non-transitory computer-readable medium for producing a signal for activating and deactivating said at least one liquid crystal film by means of said at least one power dimmer apparatus;
   2. retrofitting/mounting/attaching/adhering/laminating/allocating said at least one liquid crystal film on the surface of said vehicle; and
   3. activating said non-transitory computer-readable medium to execute said instructions, while in motion;

L. said method (K), wherein at least one of following is true:
   1. said instructions, when executed on said processor, perform the steps of:

i. activating and deactivating said at least one liquid crystal film at an operating frequency less than about 50 Hz; and
ii. providing that an exposure time for each said activating has a duration less than about one-half of a period of said operating frequency;
2. said step of activating of said liquid crystal film influence light transmittance through said film in any interval from about 1% to about 99% by means of said at least one power dimmer apparatus;
3. said liquid crystal film can be activated or deactivated without any frequency, thereby being used as a regular darkening device;
4. said method further comprises a step of providing at least one sensor selected from group consisting of light sensor; GPS; thermometer; tilt gauge; and any combination thereof;
5. said at least one liquid crystal film are the windows of said vehicle;
6. said vehicle is selected from a group consisting of terrestrial, aquatic, aerial, and any combination thereof;
7. said duration of said exposure time is short enough to prevent retinal slip of an image through said at least one liquid crystal film with respect to a sensing surface of a user's eye;
8. said operating frequency is fixed at an operating frequency less than about 10 Hz;
9. said exposure time is less than about 10 milliseconds;
10. said at least one liquid crystal film is characterized by a liquid crystal dispersion morphology in polymer matrix of nano-droplets, micro-droplets, macro-droplets or polymer network;
11. said at least one liquid crystal film is characterized by the possibility of containing dichroic organic, metal-organic and inorganic dyes;
12. said at least one liquid crystal film is characterized by the possibility of containing metallized films with static solar-reflection mode;
13. said at least one liquid crystal film is characterized by the possibility of containing broad-band cholesteric materials for dynamic solar-reflection mode;
14. said at least one liquid crystal film comprises a low-definition display or signage;
15. said at least one liquid crystal film comprises bistable capabilities;
16. said visual cues are selected from the group consisting of: lines; dots; geometrical shapes; waves; and any combination thereof;
17. said visual cues are adapted to be seen by the peripheral vision of said at least one passenger; said visual cues are adapted to be seen by the peripheral vision of said at least one passenger; or
18. said step of activating is defined by the minimal activation of stimuli necessary to provide said subject with at least one MSAQ scale point less than the corresponding subject without activating the system under the same conditions;

M. said method is provided useful for treating or preventing motion sickness to at least one passenger in a moving vehicle and comprising the steps of:
1. providing:
i. at least one liquid crystal film being operable for providing a visual cue to said at least one passenger;
ii. at least one power dimmer apparatus operative to provide AC current to said at least one liquid crystal film; and
iii. a non-transitory computer-readable medium for producing a signal for activating and deactivating said at least one liquid crystal film by means of said at least one power dimmer apparatus;
2. connecting at least one video camera to said at least one non-transitory computer-readable medium; and said at least one non-transitory computer-readable medium further comprises facial recognition instructions thereon, that when executed on said processor, by performing steps of:
i. locating the face and eyes of said at least one passenger;
ii. evaluating directionality of said face and said eyes;
iii. if directionality is away from window, then activate said liquid crystal film; and
iv. if directionality is to the window, then deactivate said liquid crystal film;
3. retrofitting/mounting/attaching/adhering/laminating/allocating said at least one liquid crystal film on the surface of said vehicle; and
4. activating said non-transitory computer-readable medium to execute said instructions, while in motion;

N. said method (M), wherein at least one of the following is true:
1. said instructions, when executed on said processor, perform the steps of:
i. activating and deactivating said at least one liquid crystal film at an operating frequency less than about 50 Hz; and
ii. providing that an exposure time for each said activating has a duration less than about one-half of a period of said operating frequency;
2. said step of activating of said liquid crystal film influence light transmittance through said film in any interval from about 1% to about 99% by means of said at least one power dimmer apparatus;
3. said liquid crystal film can be activated or deactivated without any frequency, thereby being used as a regular darkening device;
4. said method further comprises a step of providing at least one sensor selected from group consisting of light sensor; GPS; thermometer; tilt gauge; and any combination thereof;
5. said at least one liquid crystal film are the windows of said vehicle;
6. said vehicle is selected from a group consisting of terrestrial, aquatic, aerial, and any combination thereof;
7. said duration of said exposure time is short enough to prevent retinal slip of an image through said at least one liquid crystal film with respect to a sensing surface of a user's eye;
8. said operating frequency is fixed at an operating frequency less than about 10 Hz;
9. said exposure time is less than about 10 milliseconds;
10. said at least one liquid crystal film is characterized by a liquid crystal dispersion morphology in polymer matrix of nano-droplets, micro-droplets, macro-droplets or polymer network;
11. said at least one liquid crystal film is characterized by the possibility of containing dichroic organic, metal-organic and inorganic dyes;

12. said at least one liquid crystal film is characterized by the possibility of containing metallized films with static solar-reflection mode;
13. said at least one liquid crystal film is characterized by the possibility of containing broad-band cholesteric materials for dynamic solar-reflection mode;
14. at least one liquid crystal film comprises a low-definition display or signage;
15. said at least one liquid crystal film comprises bistable capabilities;
16. said visual cues are selected from the group consisting of: lines; dots; geometrical shapes; waves; and any combination thereof;
17. said visual cues are adapted to be seen by the peripheral vision of said at least one passenger; or
18. said step of activating is defined by the minimal activation of stimuli necessary to provide said subject with at least one MSAQ scale point less than the corresponding subject without activating the system under the same conditions;

O. said method is provided useful for presenting at least one motion cue to at least one passenger's peripheral vision system and comprising the steps of:
1. providing:
   i. at least one liquid crystal film;
   ii. at least one power dimmer apparatus operative to provide AC current to said at least one liquid crystal film;
   iii. at least one sensor operative to sense the motion of said vehicle;
   iv. at least one non-transitory computer-readable medium for producing a signal for activating and deactivating said at least one liquid crystal film at a certain frequency by means of said at least one power dimmer apparatus, said at least one non-transitory computer-readable medium comprising instructions thereon executed on a processor;
2. retrofitting/mounting/attaching/adhering/laminating/allocating said at least one liquid crystal film on the surface of said vehicle; and
3. activating said non-transitory computer-readable medium to execute the following instructions while in motion:
   i. receiving motion sensory inputs from said at least one sensor;
   ii. identifying the peripheral vision areas of said at least one passenger; and
   iii. activating and deactivating said at least one liquid crystal film in the form of visual cues according to said motion sensory inputs only in said peripheral vision areas of said at least one passenger;

P. said method (O), wherein at least one of the following is true:
1. said peripheral vision areas are from about 30 degrees to about 110 degrees apart from the center of the eye;
2. said method further comprising step of providing at least one sensor operative to sense the directionality of the gaze of said at least one passenger;
3. wherein said step of identifying the peripheral vision areas of said at least one passenger further comprises a step of evaluating the directionality of the gaze of said at least one passenger;
4. said directionality of the gaze of said at least one passenger together with the identified peripheral vision areas determine said activating and deactivating of said at least one liquid crystal film;
5. said non-transitory computer-readable medium further comprises instructions for activating and deactivating said at least one liquid crystal film when said directionality of said gaze of said at least one passenger is not towards the window of said vehicle;
6. wherein said step of activating of said liquid crystal film influence light transmittance through said film in any interval from about 1% to about 99% by means of said at least one power dimmer apparatus;
7. said liquid crystal film can be activated or deactivated without any frequency, thereby being used as a regular darkening device;
8. method further comprises a step of providing at least one sensor selected from group consisting of light sensor; GPS; thermometer; tilt gauge; and any combination thereof;
9. said at least one liquid crystal film are the windows of said vehicle;
10. said vehicle is selected from a group consisting of terrestrial, aquatic, aerial, and any combination thereof;
11. the duration of the exposure time is short enough to prevent retinal slip of an image through said at least one liquid crystal film with respect to a sensing surface of a user's eye;
12. said frequency is at an operating frequency from about 1 Hz to about 1000 Hz;
13. said exposure time is less than about 10 milliseconds;
14. said at least one liquid crystal film is characterized by a liquid crystal dispersion morphology in polymer matrix of nano-droplets, micro-droplets, macro-droplets or polymer network;
15. said at least one liquid crystal film is characterized by the possibility of containing dichroic organic, metal-organic and inorganic dyes;
16. said at least one liquid crystal film is characterized by the possibility of containing metallized films with static solar-reflection mode;
17. said at least one liquid crystal film is characterized by the possibility of containing broad-band cholesteric materials for dynamic solar-reflection mode;
18. said at least one liquid crystal film comprises a low-definition display or signage;
19. said at least one liquid crystal film comprises bistable capabilities; or
20. said step of activating is defined by the minimal activation of stimuli necessary to provide said subject with at least one MSAQ scale point less than the corresponding subject without activating the system under the same conditions.

9. The method of claim 8, wherein A. said method is provided useful by translating sensed motion of a vehicle into motion cues perceived by at least one passenger, and comprising the steps of:
1. providing:
   i. at least one liquid crystal film;
   ii. at least one power dimmer apparatus operative to provide AC current to said at least one liquid crystal film;
   iii. at least one sensor operative to sense the motion of said vehicle; and
   iv. at least one non-transitory computer-readable medium for producing a signal for activating and deactivating said at least one liquid crystal film in a certain frequency by means of said at least one power dimmer apparatus, said at least one non-transitory computer-readable medium comprising instructions thereon executed on a processor;
2. retrofitting/mounting/attaching/adhering/laminating/allocating said at least one liquid crystal film on the surface of said vehicle; and
3. activating said non-transitory computer-readable medium to execute the following instructions while in motion:
   i. receiving motion sensory inputs from said at least one sensor; and
   ii. activating and deactivating said at least one liquid crystal film in the form of visual cues according to said motion sensory inputs.

10. The method of claim 8, wherein C. said method comprises the steps of:
1. providing:
   i. at least one liquid crystal film;
   ii. at least one power dimmer apparatus operative to provide AC current to said at least one liquid crystal film;
   iii. at least one sensor operative to sense the motion of said vehicle; and
   iv. at least one non-transitory computer-readable medium for producing a signal for activating and deactivating said at least one liquid crystal film at a certain frequency by means of said at least one power dimmer apparatus, said at least one non-transitory computer-readable medium comprising instructions thereon executed on a processor;
2. retrofitting/mounting/attaching/adhering/laminating/allocating said at least one liquid crystal film on the surface of said vehicle; and
3. activating said non-transitory computer-readable medium to execute the following instructions while in motion:
   i. receiving motion sensory inputs from said at least one sensor; and
   ii. activating and deactivating said at least one liquid crystal film in the form of visual cues according to said motion sensory inputs.

11. The method of claim 8, wherein E. said method is provided useful for presenting at least one motion cue to at least one passenger's peripheral vision system; said method comprising the steps of:
1. providing:
   i. at least one liquid crystal film;
   ii. at least one power dimmer apparatus operative to provide AC current to said at least one liquid crystal film;
   iii. at least one sensor operative to sense the motion of said vehicle;
   iv. at least one sensor operative to sense the directionality of the gaze of said at least one passenger; and
   v. at least one non-transitory computer-readable medium for producing a signal for activating and deactivating said at least one liquid crystal film by means of said at least one power dimmer apparatus, said at least one non-transitory computer-readable medium comprising instructions thereon executed on a processor;
2. retrofitting/mounting/attaching/adhering/laminating/allocating said at least one liquid crystal film on the surface of said vehicle; and
3. activating said non-transitory computer-readable medium to execute the following instructions while in motion:
   i. receiving motion sensory inputs from said at least one sensor;
   ii. activating and deactivating said at least one liquid crystal film in the form of visual cues according to said motion sensory inputs; and
   iii. activating and deactivating said at least one liquid crystal film when said directionality of said gaze of said at least one passenger is not towards the window of said vehicle.

12. The method of claim 8, wherein G. said method is provided useful for minimizing the effect on lightning inside a vehicle due to flickering of an anti-motion sickness system, said anti-motion sickness system comprising at least one liquid crystal film; at least one power dimmer apparatus operative to provide AC current to said at least one liquid crystal film; at least one non-transitory computer-readable medium for producing a signal for activating and deactivating said at least one liquid crystal film in a certain frequency by means of said at least one power dimmer apparatus; said method comprising the steps of:
1. providing:
   i. at least one lightning sensor; and
   ii. at least one non-transitory computer-readable medium;
2. activating said non-transitory computer-readable medium to execute the following instructions while said anti-motion sickness system is active:
3. setting the desired lightning conditions in said vehicle; and
4. modifying at least one parameter of the activation of said anti-motion sickness system, selected from the group consisting of: frequency, light transmittance through the film, voltage, transparency, phase shift, and any combination thereof; as to reach said desired lightning conditions in said vehicle.

13. The method of claim 8, wherein I. said method is provided useful for preventing motion sickness to at least one passenger in a moving vehicle, comprising the steps of:
1. providing:
   i. at least one liquid crystal film being operable for partially blocking vision to at least one eye of at least one user through said at least one liquid crystal film by activating said at least one liquid crystal film, said at least one liquid crystal film being operable for simultaneously permitting vision to both eyes of at least one user through said at least one liquid crystal film by deactivating said at least one liquid crystal film;
   ii. at least one power dimmer apparatus operative to provide AC current to said at least one liquid crystal film; and
   iii. a non-transitory computer-readable medium, comprising a processor, for producing a signal for activating and deactivating said at least one liquid crystal film by means of said at least one power dimmer apparatus;
2. retrofitting/mounting/attaching/adhering/laminating/allocating said at least one liquid crystal film on the surface of said vehicle; and
3. activating said non-transitory computer-readable medium to execute instructions while in motion.

14. The method of claim 8, wherein K. said method is for treating or preventing motion sickness to at least one passenger in a moving vehicle, comprising the steps of:
1. providing:
   i. at least one liquid crystal film being operable for providing a visual cue to said at least one passenger;

ii. at least one power dimmer apparatus operative to provide AC current to said at least one liquid crystal film; and
  iii. a non-transitory computer-readable medium for producing a signal for activating and deactivating said at least one liquid crystal film by means of said at least one power dimmer apparatus;
2. retrofitting/mounting/attaching/adhering/laminating/allocating said at least one liquid crystal film on the surface of said vehicle; and
3. activating said non-transitory computer-readable medium to execute said instructions, while in motion.

15. The method of claim 8, wherein M. said method is provided useful for treating or preventing motion sickness to at least one passenger in a moving vehicle and comprising the steps of:
  1. providing:
    i. at least one liquid crystal film being operable for providing a visual cue to said at least one passenger;
    ii. at least one power dimmer apparatus operative to provide AC current to said at least one liquid crystal film; and
    iii. a non-transitory computer-readable medium for producing a signal for activating and deactivating said at least one liquid crystal film by means of said at least one power dimmer apparatus;
  2. connecting at least one video camera to said at least one non-transitory computer-readable medium; and said at least one non-transitory computer-readable medium further comprises facial recognition instructions thereon, that when executed on said processor, by performing steps of:
    i. locating the face and eyes of said at least one passenger;
    ii. evaluating directionality of said face and said eyes;
    iii. if directionality is away from window, then activate said liquid crystal film; and
    iv. if directionality is to the window, then deactivate said liquid crystal film;
  3. retrofitting/mounting/attaching/adhering/laminating/allocating said at least one liquid crystal film on the surface of said vehicle; and
  4. activating said non-transitory computer-readable medium to execute said instructions, while in motion.

16. The method of claim 8, wherein O. said method is provided useful for presenting at least one motion cue to at least one passenger's peripheral vision system and comprising the steps of:
  1. providing:
    i. at least one liquid crystal film;
    ii. at least one power dimmer apparatus operative to provide AC current to said at least one liquid crystal film;
    iii. at least one sensor operative to sense the motion of said vehicle;
    iv. at least one non-transitory computer-readable medium for producing a signal for activating and deactivating said at least one liquid crystal film at a certain frequency by means of said at least one power dimmer apparatus, said at least one non-transitory computer-readable medium comprising instructions thereon executed on a processor;
  2. retrofitting/mounting/attaching/adhering/laminating/allocating said at least one liquid crystal film on the surface of said vehicle; and
  3. activating said non-transitory computer-readable medium to execute the following instructions while in motion:
    i. receiving motion sensory inputs from said at least one sensor;
    ii. identifying the peripheral vision areas of said at least one passenger; and
    iii. activating and deactivating said at least one liquid crystal film in the form of visual cues according to said motion sensory inputs only in said peripheral vision areas of said at least one passenger.

* * * * *